United States Patent
Zook et al.

(10) Patent No.: US 10,172,642 B2
(45) Date of Patent: Jan. 8, 2019

(54) METHOD FOR PLACING A CANNULA IN A BLADDER

(71) Applicant: SWAN VALLEY MEDICAL INCORPORATED, Bigfork, MT (US)

(72) Inventors: Ronald E. Zook, Bigfork, MT (US); Laurence K. Sampson, Greenwood Village, CO (US); Mark Carl, Denver, CO (US)

(73) Assignee: SWAN VALLEY MEDICAL INCORPORATED, Bigfork, MT (US)

( * ) Notice: Subject to any disclaimer, the term of this patent is extended or adjusted under 35 U.S.C. 154(b) by 367 days.

(21) Appl. No.: 15/002,156

(22) Filed: Jan. 20, 2016

(65) Prior Publication Data
US 2016/0135837 A1  May 19, 2016

Related U.S. Application Data

(62) Division of application No. 13/801,288, filed on Mar. 13, 2013, now Pat. No. 9,271,752.

(51) Int. Cl.
| | |
|---|---|
| *A61B 17/34* | (2006.01) |
| *A61M 29/02* | (2006.01) |
| *A61B 17/02* | (2006.01) |

(52) U.S. Cl.
CPC ...... *A61B 17/3423* (2013.01); *A61B 17/0218* (2013.01); *A61B 17/3403* (2013.01); *A61B 17/3415* (2013.01); *A61B 17/3421* (2013.01); *A61M 29/02* (2013.01); *A61B 2017/3405* (2013.01); *A61B 2017/346* (2013.01); *A61B 2017/3486* (2013.01)

(58) Field of Classification Search
CPC ............ A61B 17/3417; A61B 17/0057; A61B 17/34; A61B 17/3401; A61B 17/3462; A61B 17/3431; A61B 17/3439; A61B 17/3476; A61B 17/3423; A61B 17/0218; A61B 17/3421; A61B 17/3403; A61B 17/3415; A61B 2017/3419; A61B 2017/0023; A61B 2017/3425; A61B 2017/3427; A61B 2017/3429; A61B 2017/3433; A61B 2017/3447; A61B 2017/3435; A61B 2017/3407; A61B 2017/3409; A61B 2017/348; A61B 2017/3484; A61B 2017/349; A61B 2017/3492; A61B 2017/0243; A61B 2017/3486; A61B 2017/346; A61B 2017/3405; A61B 18/1487; A61B 10/0233; A61M 2029/025; A61M 29/02
See application file for complete search history.

(56) References Cited

U.S. PATENT DOCUMENTS

| | | | | |
|---|---|---|---|---|
| 5,019,032 | A * | 5/1991 | Robertson | A61B 17/0469 128/898 |
| 5,183,464 | A * | 2/1993 | Dubrul | A61M 25/0023 604/104 |

* cited by examiner

Primary Examiner — Eric Rosen
Assistant Examiner — Chima Igboko
(74) Attorney, Agent, or Firm — Robert G. Crouch; Marsh Fischmann & Breyfogle LLP

(57) ABSTRACT

A cannula is placed in an enlarged opening through a bladder wall and an abdominal wall by applying pulling tension to a placement guide extending through a small pathway to hold an inflated placement balloon in sealing contact with the bladder wall. The seal confines distension fluid in the bladder to establish sufficient reactive resistance to enlarge the opening through the bladder wall with blunt force dilation from an obturator.

20 Claims, 26 Drawing Sheets

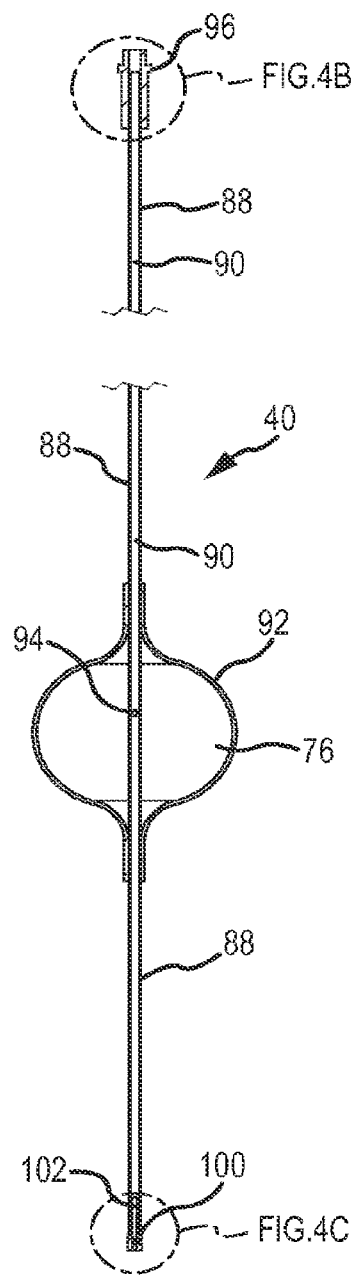
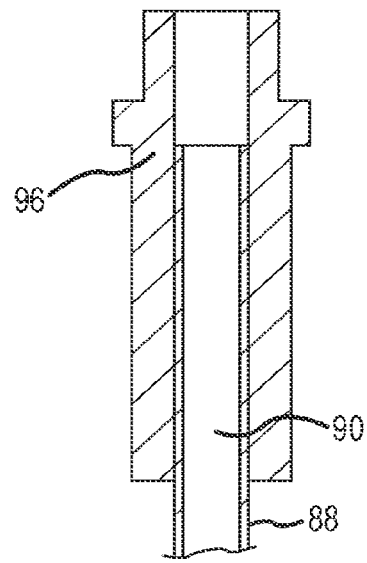
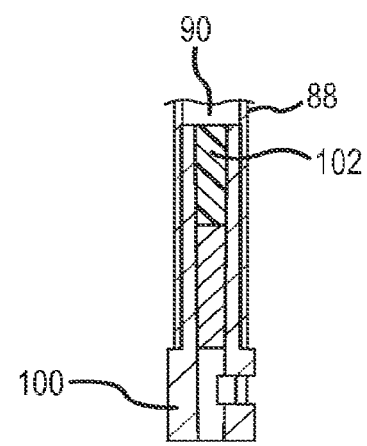
FIG.4B
FIG.4C
FIG.4A

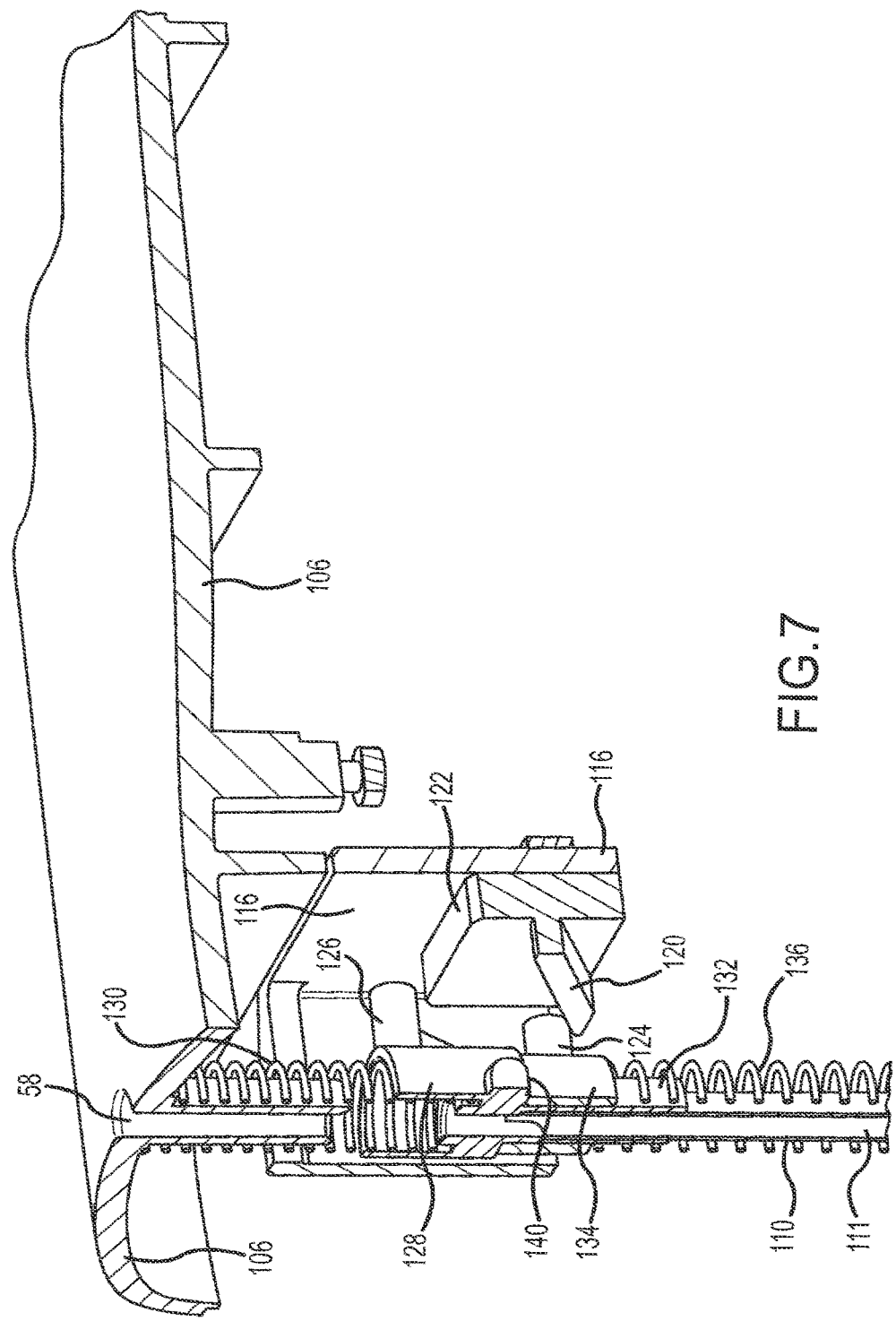

METHOD FOR PLACING A CANNULA IN A BLADDER

CROSS REFERENCE TO RELATED APPLICATIONS

This application is a divisional of U.S. patent application Ser. No. 13/801,288, filed on Mar. 13, 2013, which is incorporated herein in its entirety by reference.

This invention relates to minimally invasive surgical procedures, and more particularly to such surgical procedures performed within a bladder of a living being. Even more particularly, the present invention relates to a new and improved method and apparatus for placing a cannula in the bladder by which to access the bladder to perform the surgical procedure. The method and apparatus significantly improve the reliability of placing the cannula in the bladder without inadvertently damaging adjoining organs and tissue, reduces the number of actions required by the surgeon, and facilitates progression of the procedure, among other things.

BACKGROUND OF THE INVENTION

Minimally invasive surgery is a surgical procedure performed by making a very small incision through which to insert surgical instruments to perform the surgical procedure. A minimally invasive procedure is usually performed in the abdominal region, by inserting a cannula through an abdominal wall of the patient. The cannula provides access to the surgical site for inserting, manipulating and removing the surgical instruments at the interior surgical site. Minimally invasive surgery substantially reduces the amount of trauma to a patient compared to a completely open surgical procedure in which a large incision is made to directly visualize and contact the tissue that the surgical site. In most cases, the time for the patient to recover from the surgery is substantially reduced. In urological surgery performed on or in the bladder, minimally invasive surgery avoids a substantial incision in the wall of the bladder which will complicate and prolong healing.

A dilation instrument, such as a trocar or obturator, is commonly used to place the cannula within the abdominal wall. The trocar or obturator is used to expand an initial small surgical pathway through the abdominal wall into a wider opening to accommodate the larger cannula. The typical dilation procedure involves forcing the trocar or obturator through the small surgical pathway to expand or spread the tissue surrounding the small surgical pathway into the enlarged opening for the cannula. Once the enlarged opening has been formed, the cannula is inserted and the trocar or obturator is removed, leaving a relatively large pathway through the cannula for inserting, manipulating and removing the medical instruments.

Significant physical force is required to spread the surrounding tissue when expanding the small surgical pathway into the enlarged opening. Typically, the leading end of the trocar or the obturator has a pointed or flared configuration which expands the tissue when physically forced through the small surgical pathway. This expansion technique is known as blunt force dilation.

Blunt force dilation usually requires a considerable amount of pushing force to create the enlarged opening. Considerable force is required because the tough, relatively non-expandable characteristics of the exterior skin on the abdominal wall and of a fascia layer located at the internal margin of the abdominal wall creates substantial resistance to expansion of the tissue surrounding the small surgical pathway. A layer of mostly vascular and adipose tissue separates the exterior skin and the interior fascia layer in the abdominal wall, but this intermediate portion does not generally create substantial resistance to expansion. The physically tough and relatively nonexpandable characteristics of the exterior skin and the interior fascia layer are responsible for the considerable force required to accomplish blunt force dilation through the abdominal wall.

To diminish the force necessary to penetrate the exterior skin layer, small enlarging cuts radial cuts are made in the exterior skin surrounding the initial small pathway, usually with a scalpel. However, making similar manual cuts the interior fascia layer is more difficult and engenders significant risks, because such cuts may extend beyond the internal fascia layer into adjacent internal organs and damage those organs. In most cases with minimally invasive surgery in the abdominal area, insufflation expands the abdominal wall away from the adjacent internal organs and tissues sufficiently so that penetrating the internal fascia layer with blunt force dilation usually carries no attendant risk of damaging adjoining internal organs.

Some types of trocars and obturators have cutting surfaces or blades formed on their leading tips to facilitate cutting from the outside through the abdominal wall, including the internal fascia layer. Using trocars and obturators with cutting surfaces and blades carries the risk of unintended deeper penetration into and damage of adjoining internal organs. The considerable force required to break through the internal fascia layer may propel the tip of the trocar or obturator into the adjoining organs when breakthrough of the fascia layer occurs. Even with blunt tip trochars and obturators that do not have cutting surfaces or blades, there is a risk of damage to the adjacent internal organs.

To accomplish minimally invasive bladder surgery, it is necessary to penetrate the bladder wall to gain access to the interior of the bladder. Penetrating the bladder wall with a trocar or obturator is difficult because the bladder wall is very flaccid and easily deformable and movable. The bladder wall offers very little reactive resistance to force applied during blunt force dilation, regardless of whether or not a small surgical pathway has been made initially through the bladder wall. In response to blunt dilation force, it is typical that the bladder wall depresses and moves away from the tip of the trocar or obturator and/or deflect sideways from the initial position, even when the initial small surgical pathway has been formed in the bladder wall. The lack of significant reactive resistance from the bladder wall itself makes it is very difficult to penetrate the bladder wall from the outside to the inside of the bladder, which of course is the direction of penetration for enlarging the opening to insert the cannula. Even when penetration is achieved, that penetration may occur in a location different from that desired or at a location separated from the initial small surgical incision, due to the sideways deflection of the bladder wall.

To attempt to make the bladder wall more resistant to deflection and sideways movement, the bladder may be filled with fluid to distend the bladder wall. The distension fluid creates a reactive resistance to movement of the bladder wall, and allows penetration to be more effectively accomplished at the desired location. However, making an initial small surgical pathway or incision through the bladder wall prior to expanding that small pathway causes the distention fluid to leak from the bladder, thereby losing most of the benefit derived from fluid distention.

U.S. Pat. No. 8,118,826, which is assigned to the assignee hereof, describes an advantageous procedure for making an initial small surgical pathway starting inside the bladder and progressing outward through the bladder wall and the abdominal wall to the external skin. Such an inside-out incision is relatively more controllable because the bladder wall is pushed against the more reactively resistant abdominal wall. A cutting element readily pierces through the bladder wall and the abdominal wall to create the initial small surgical pathway. However, if the initial alignment of the surgical pathway through the bladder wall and the abdominal wall is lost, as it will be if the advancement member which makes the inside-out initial small surgical pathway is withdrawn from that pathway, it is virtually impossible to regain the alignment of the small pathways through the bladder wall and the abdominal wall to facilitate enlarging the small pathway with outside-in blunt force dilation. Attempts to regain the alignment are resisted by the flaccid nature of the bladder wall which easily shifts sideways relative to the location of the small pathway in the more stable abdominal wall. Under such circumstances, when penetration of the bladder wall is finally achieved, the penetration may occur in a different position from the small surgical pathway initially made through the bladder wall.

Thus, forming the initial small surgical pathway through the bladder wall does not facilitate enlargement of that opening, but instead may result in creating an extra opening through the bladder wall. Even if the alignment of the initial surgical pathways through the bladder wall and abdominal wall is maintained, the flaccid nature of the bladder wall may cause it to deform in response to the blunt force from a trocar or obturator, thereby distorting the location of the enlarged opening in the bladder wall.

SUMMARY OF THE INVENTION

This invention involves a method and apparatus which are used very effectively to place a cannula through the abdominal wall and the bladder wall. An initial small surgical pathway, preferably made inside-out from the bladder through the bladder wall and the abdominal wall to the exterior skin, is expanded by outside-in force applied by an obturator, while the flaccid bladder wall is held firmly by reactive resistance created by fluid distention of the bladder. An effective seal within the bladder around the initial small surgical pathway is established before the obturator is used, thereby causing the distention fluid to offer enough reactive resistance to maintain the flaccid bladder wall in a firm condition conducive to blunt force dilation. The small pathway through the flaccid bladder wall is maintained in alignment with the small pathway through the firmer abdominal wall. With the bladder wall retained by the reactive resistance caused by fluid distention and with the small pathways through the bladder and abdominal walls in alignment, the small surgical pathway is effectively enlarged by an obturator around which a cannula is temporarily connected. The cannula is placed in the enlarged opening as a part of the same action which enlarges the small surgical pathway, thereby avoiding risks of losing alignment of the enlarged openings through the abdominal wall and the bladder wall if the cannula was inserted separately.

Penetration of the obturator through the internal fascia layer of the abdominal wall is achieved with the assistance from small cuts made by retractable blades at the forward end of the obturator. Substantial pushing force from the surgeon is not required, thereby avoiding risks that substantial pushing force may inadvertently damage adjoining internal organs or the opposite wall of the bladder. After penetrating the internal fascia layer, the small pathway through the bladder wall is expanded relatively easily by blunt force dilation while the flexible bladder wall is held firmly by the reactive resistance of the distending fluid within the bladder. The surgeon achieves enhanced control over the surgical procedure, which allows the surgical procedure to progress more rapidly with less trauma to the patient.

In accordance with these and other considerations and improvements, one aspect of the invention relates to a method of enlarging a small surgical pathway through the bladder wall and the abdominal wall and placing a cannula in the enlarged opening through a bladder wall and an abdominal wall by which to access to the interior of the bladder from the exterior of the abdominal wall. The method involves extending an elongated placement guide through the small surgical pathway until a forward end of the placement guide is located within the bladder, inflating a placement balloon on the forward end of the placement guide within the bladder, applying pulling tension to the placement guide at the exterior of the abdominal wall to move the inflated placement balloon into contact with the bladder wall adjacent to the small surgical pathway and create a seal around the small surgical pathway, distending the bladder wall with fluid introduced into the bladder while the placement balloon seals the small surgical pathway to hold the distention fluid within the bladder, enlarging the small surgical pathway into the enlarged opening while applying pulling tension on the placement guide, and inserting the cannula through the enlarged opening.

Additional features of this aspect of the invention involve some or all of the following. The small surgical pathway is enlarged into the enlarged opening by guiding an obturator along the placement guide and through the abdominal wall and the bladder wall. The obturator and the cannula are connected as a unit and guided along the placement guide and through the abdominal wall and the bladder wall. Cutting the exterior of the abdominal wall facilitates moving the unit-connected obturator and cannula through the exterior skin of the abdominal wall. Cutting the internal fascia layer of the abdominal wall by a blade which is selectively extended from a forward end of the obturator facilitates moving the obturator and cannula through the internal fascia layer. The opening through the bladder wall is expanded by blunt tip dilation after retracting the blade into the forward end of the obturator. The pulling tension on the placement guide is relaxed to allow the inflated placement balloon on the forward end of the placement guide to move out of contact with the bladder wall as the forward end of the obturator moves through the bladder wall. A stabilization balloon on the forward end of the cannula is inflated within the bladder and the cannula is withdrawn until the expanded stabilization balloon contacts of the bladder wall adjacent to the expanded opening. The obturator and placement guide are removed from within a conduit of the cannula after deflating the placement balloon on the forward end of the placement guide and disconnecting the obturator from the cannula. A retainer on the exterior of the conduit of the cannula contacts the abdominal wall at the enlarged opening while the expanded stabilization balloon contacts the bladder wall adjacent to the expanded opening, to maintain and stabilize the cannula within the expanded opening. The small surgical pathway through the bladder wall and the abdominal wall is preferably created by extending an advancement member from an end of a sound inserted through the urethra into the bladder, and the placement guide is extended through the small surgical pathway by connecting a forward end of the placement guide to a forward end of the advancement member and withdrawing the advancement member and the sound until the forward end of the placement guide is located in the bladder. The placement balloon is located in the bladder by severing the forward end of the placement guide from the forward end of the advancement member after both have been withdrawn through the urethra, and then returning the forward end of the placement guide into the bladder.

Another aspect of the invention relates to apparatus for placing a cannula in an enlarged opening through a bladder wall and an abdominal wall. The apparatus comprises a placement guide, an obturator and the cannula. The cannula has a conduit which defines a central channel that provides access through the cannula. The placement guide comprises an elongated flexible guide tube having a flexible membrane at a forward end which expands into a placement balloon. The obturator comprises a hollow obturator shaft and at least one blade. Each blade is positioned at a forward end of the obturator shaft. Each blade moves between an extended position where it projects outward from the forward end of the obturator shaft and a retracted position where each blade withdraws into the forward end of the obturator shaft. An actuation member is movably positioned within the obturator shaft to extend and retract each blade. A selectively actuatable activation mechanism in a housing of the obturator moves the actuation member to move each blade between the extended and retracted positions. The obturator and the cannula are selectively connectable as a unit with the obturator shaft extending through the central channel and the conduit of the cannula, and the blade is located beyond the forward end of the cannula. A center passage extends in the obturator housing and through the obturator shaft to the forward end of the obturator shaft. The placement guide is inserted in the center passage until the forward end of the guide tube extends forward from the forward end of the obturator shaft and with the rear end of the guide tube extends rearward from the housing. The center passage guides the connected obturator and cannula along the guide tube. Each blade moves between the extended and retracted positions while the guide tube is positioned in the center passage.

Additional features of this aspect of the invention involve some or all of the following. Each extended blade avoids contact with the placement balloon when the guide tube is located within the center passage and the placement balloon is positioned adjacent to the forward end of the obturator shaft. The actuation member comprises a hollow actuation tube having a center opening within which the guide tube is positioned. The center passage includes open center of the actuation tube, and the actuation mechanism moves the actuation tube axially to extend and retract the blade. The cannula includes a flexible membrane at a forward end of the of the conduit which expands as a stabilization balloon to contact the bladder wall within the bladder. A retainer on the conduit contacts the exterior skin of the abdominal wall. The stabilization balloon and the retainer maintain and stabilize the cannula in the enlarged opening. The housing of the obturator includes a handle adapted to be grasped by a hand, and an actuator button extends from the housing at a position to be depressed by a thumb of the hand that grasps the handle. Depression of the actuator button causes the actuation mechanism to move the blade to the extended position. A follower of the actuation mechanism moves along a ramp structure to move the actuation member to extend and retract the blade. The forward end of the guide tube includes a mechanical connector by which to pull the guide tube and the deformable membrane through a small surgical pathway from exterior skin of abdominal wall through the bladder wall into the bladder. The flexible membrane forms a placement balloon on the forward end of the guide tube to transfer force to hold the bladder wall adjacent to the abdominal wall when force is applied at the rear end of the guide tube at the exterior of the abdominal wall.

These and other inventive aspects are described specifically in the appended claims. A more complete appreciation of the invention, as well as the manner in which many of its improvements are obtained, is available by reference to the following detailed description of presently preferred embodiments taken in connection with the accompanying drawings, which are briefly summarized below.

BRIEF DESCRIPTION OF THE DRAWINGS

FIG. 4A is an axial section view of the placement guide shown in FIGS. 1-3, with its balloon inflated as shown in FIG. 3.

FIG. 4B is an enlarged view of a rear end of the placement guide shown in FIG. 4A, showing an inflation connector used for inflating the balloon.

FIG. 4C is an enlarged view of a forward end of the placement guide shown in FIG. 4A, showing a mechanical connector used for pulling the placement guide through a small surgical opening in the abdominal and bladder walls.

FIG. 6A is a perspective view of the forward end of the obturator with a portion broken out along an axial section to show blades in a retracted position. FIG. 6B is a perspective view of the forward end of the obturator shown in FIG. 6A with a portion broken out to show the blades in the retracted position. FIG. 6C is a perspective view of the forward end of the obturator with a portion broken out along an axial section to show the blades in an extended position. FIG. 6D is a perspective view of the forward end of the obturator shown in FIG. 6C with the blades in the extended position.

FIG. 7 is an enlarged perspective view of an upper end and housing of the obturator, taken from a perspective different from that shown in FIG. 5, and with an additional perpendicular transverse section that eliminates certain components of the housing for clarity of illustration.

FIG. 10 is a perspective view of a transurethral medical instrument having a sound inserted through the urethra and into the bladder, to locate the position for forming an inside-out initial small surgical pathway from the bladder through the bladder wall and the abdominal wall to the exterior of the abdominal wall.

FIG. 11 is view similar to FIG. 10, showing formation of the inside-out initial small surgical pathway with components of the transurethral medical instrument shown in FIG. 10.

FIG. 12 is a view similar to FIG. 11, showing the extension of an advancement member of the transurethral medical instrument through the initial surgical pathway and beyond the exterior of the abdominal wall.

FIG. 13 is a view similar to FIG. 12, showing the placement guide, obturator and cannula shown in FIGS. 1-3 after the placement guide has been connected to an end of the advancement member and then pulled through the initial surgical pathway and into the bladder by withdrawing the advancement member.

FIG. 14 is a view similar to FIG. 13, showing continued movement the placement guide and the sound of the transurethral medical instrument through the urethra until the forward end of the placement guide is located outside of the urethra. FIG. 14 also illustrates severing the placement guide from the advancement member after the forward end of the placement guide is located outside of the urethra.

FIG. 15 is a view similar to FIG. 14, showing movement of the forward end of the placement guide back into the bladder, inflation of a placement balloon on a forward end of the placement guide within the bladder, and insertion of a cystoscope through the urethra into the bladder to view the forward end of the placement guide and the inflation of the placement balloon.

FIG. 16 is a view similar to FIG. 15, showing movement of the inflated placement balloon into contact with the bladder wall and applying tension to the rear end of the placement guide at the exterior of the abdominal wall to retain the placement balloon against the bladder wall, with the obturator and cannula moved along the placement guide until a forward end of the obturator contacts the exterior skin of the abdominal wall.

FIG. 17 is a view similar to FIG. 16, showing movement of the forward end of the obturator through the exterior skin of the abdominal wall, assisted by cuts in the exterior skin of the abdominal wall, and the forward end of the obturator contacting an internal fascia layer of the abdominal wall, all while the tension is applied to the rear end of the placement guide to maintain the inflated balloon in contact with the bladder wall. FIG. 17 also shows distention of the bladder by fluid introduced into the bladder through the cystoscope.

FIG. 18 is an enlarged portion of FIG. 17 showing deployment of the blades on the forward end of the of the obturator, as shown in FIGS. 6C and 6D, to cut the internal fascia layer of the abdominal wall and allow the forward end of the obturator to penetrate the internal fascia layer with reduced force.

FIG. 19 is a view similar to FIG. 17, showing blunt force dilation of the bladder wall by the forward end of the obturator with the blades in a retracted position, while the placement balloon moves forward with the obturator as the tension in the placement guide is maintained.

FIG. 20 is a view similar to FIG. 19, showing insertion of the forward end of the obturator and the forward end of the cannula into the bladder through the enlarged opening in the bladder wall.

FIG. 21 is a view similar to FIG. 20, showing inflation of a stabilization balloon on the forward end of the cannula, contact of the inflated stabilization balloon of the cannula with the bladder wall, and contact at the exterior skin of the abdominal wall by a retainer.

FIG. 22 is a view similar to FIG. 21, showing removal of the obturator and the placement guide from within the cannula, after deflation of the balloon on the forward end of the placement guide and disconnection of the obturator from the cannula. FIG. 22 also illustrates stabilized placement of the cannula in a position of use extending through the bladder wall and the abdominal wall.

FIG. 23 is an enlarged view of the of the bladder similar to that shown in FIG. 22, illustrating the insertion of a medical instrument through the cannula in its position of use, with the cystoscope removed from the urethra.

DETAILED DESCRIPTION

Figure 1:
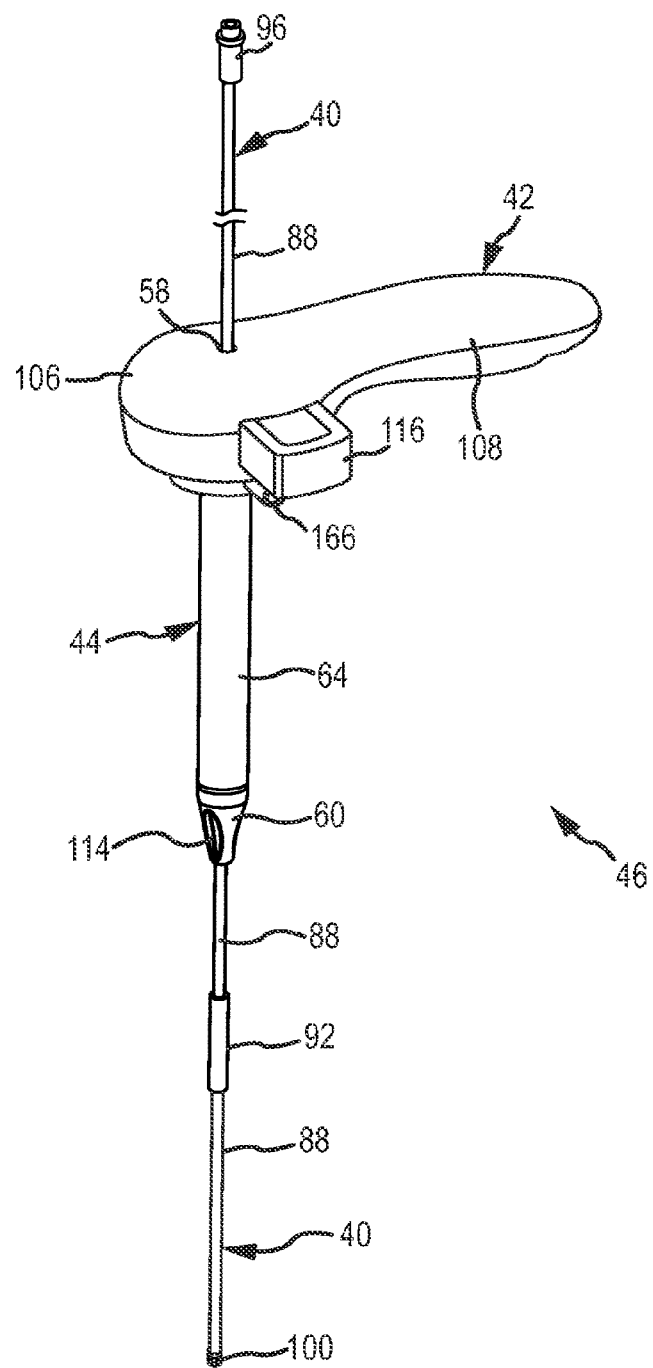
FIG. 1 is a perspective view of a placement guide, an obturator and a cannula shown in an assembled or combined relationship in the manner in which they are used to expand an initial small pathway through a bladder wall and an abdominal wall into an enlarged opening in which to place the catheter. The placement guide, obturator and cannula incorporate apparatus of the present invention.
Figure 2:
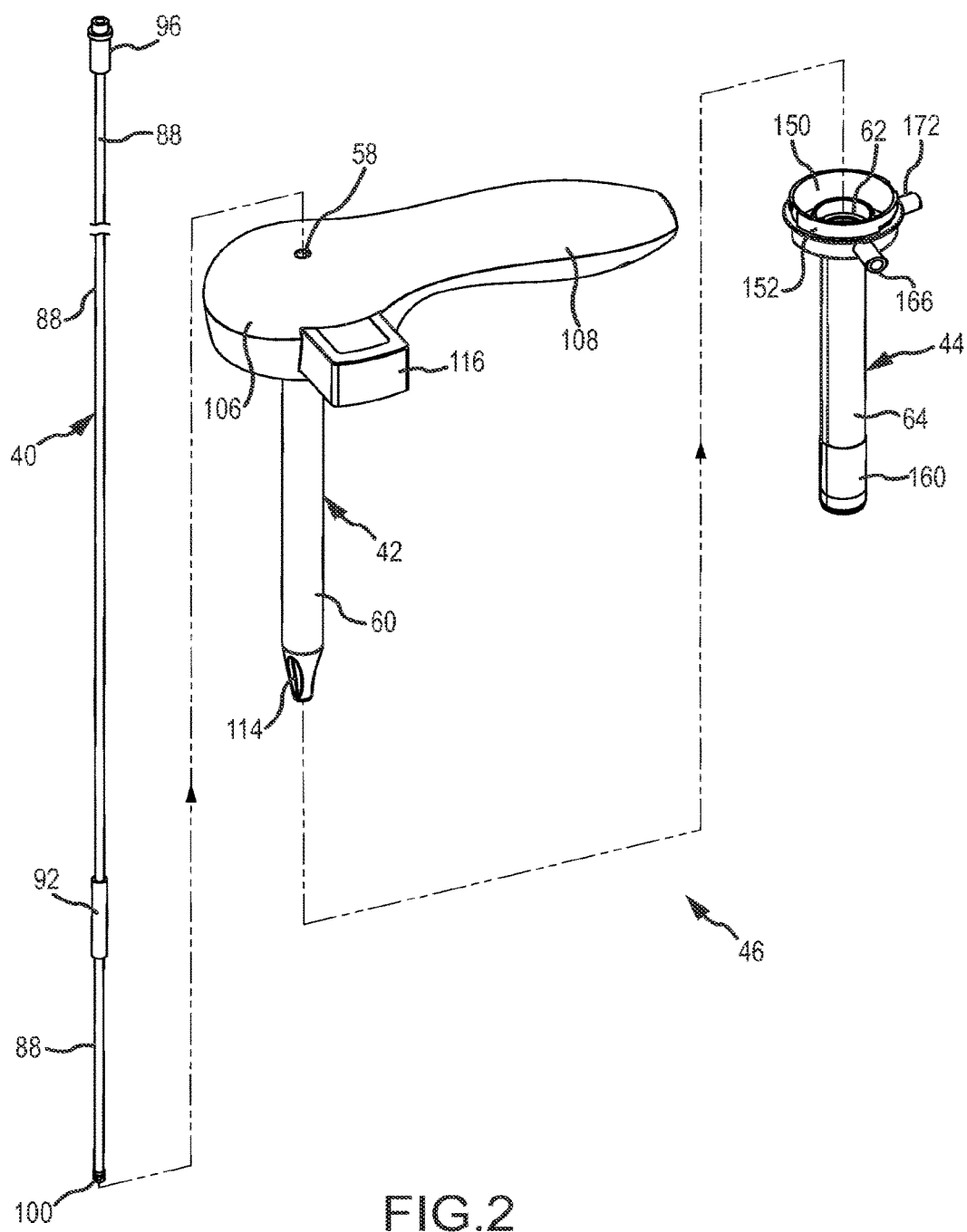
FIG. 2 is an exploded view of the placement guide, obturator and cannula shown in FIG. 1.
Figure 3:
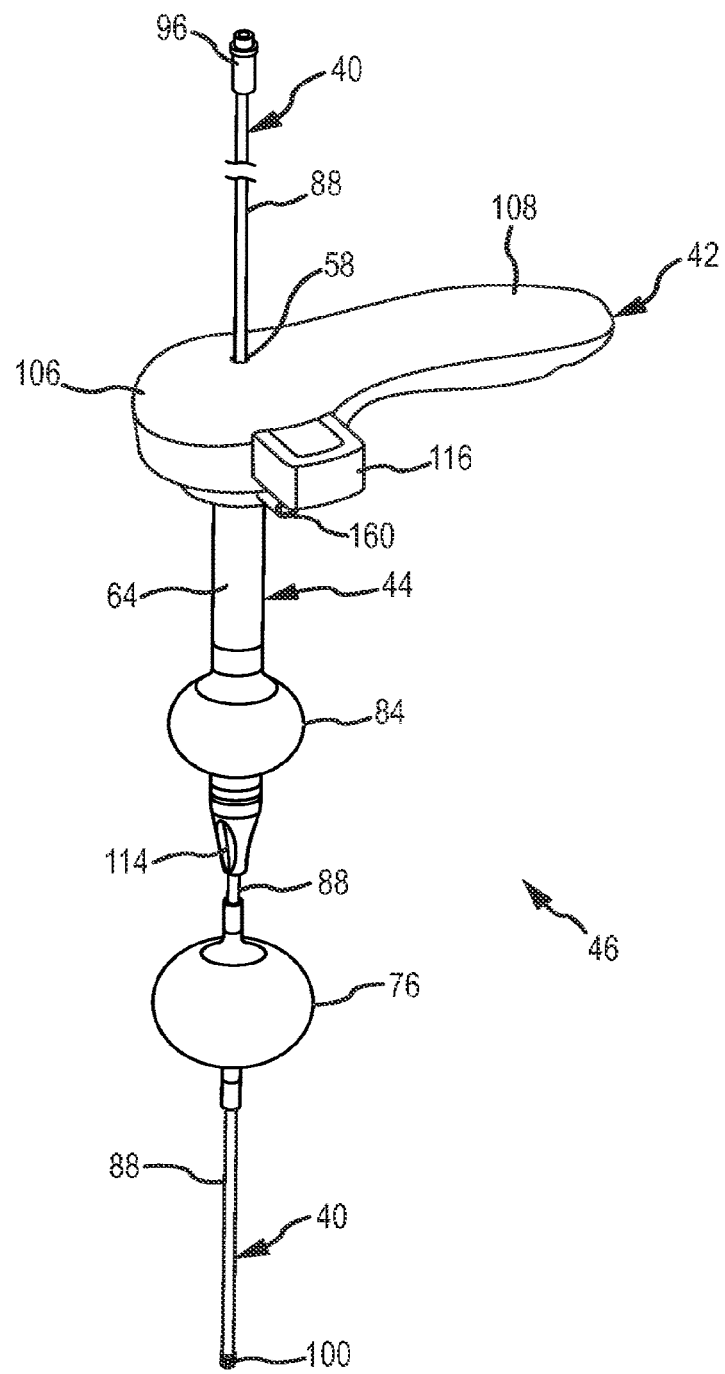
FIG. 3 is a perspective view of the placement guide, obturator and cannula shown in FIG. 1, with balloons of the placement guide and the obturator shown in an inflated condition.

A placement guide 40, an obturator 42, and a cannula 44, shown generally in FIGS. 1-3, are used together as apparatus 46 to place the cannula 44 in an enlarged opening 48 (FIGS. 19-22) extending from a bladder 50 through a bladder wall 52 and an abdominal wall 54 of a living being, shown generally in FIGS. 10-22. Once placed in the enlarged opening 48, the cannula 44 provides access for inserting medical instruments 56 into the bladder 50 to perform a minimally invasive surgical procedure (FIG. 23).

To use the apparatus 46, the placement guide 40 is inserted within a center passage 58 of the obturator 42. A shaft of 60 of the obturator 42 is inserted within a central channel 62 of an exterior conduit 64 of the cannula 44. FIG. 1 shows the assembled relationship of the placement guide 40, the obturator 42 and the cannula 44, and FIG. 2 shows their interconnected relationship.

Figure 12:
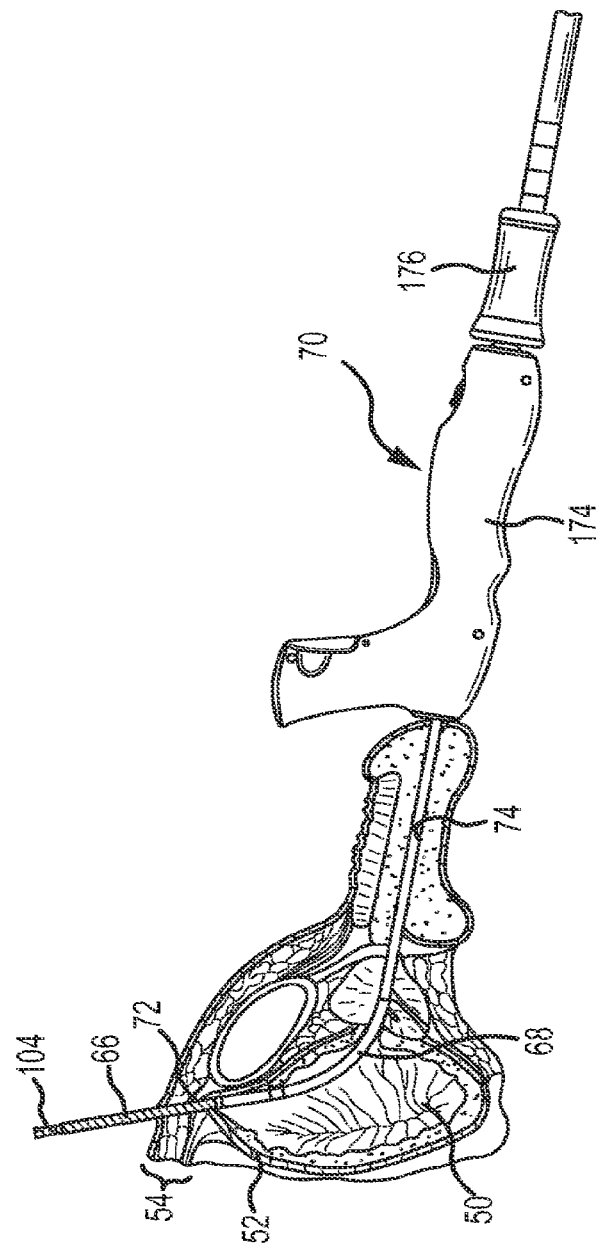
Figure 13:
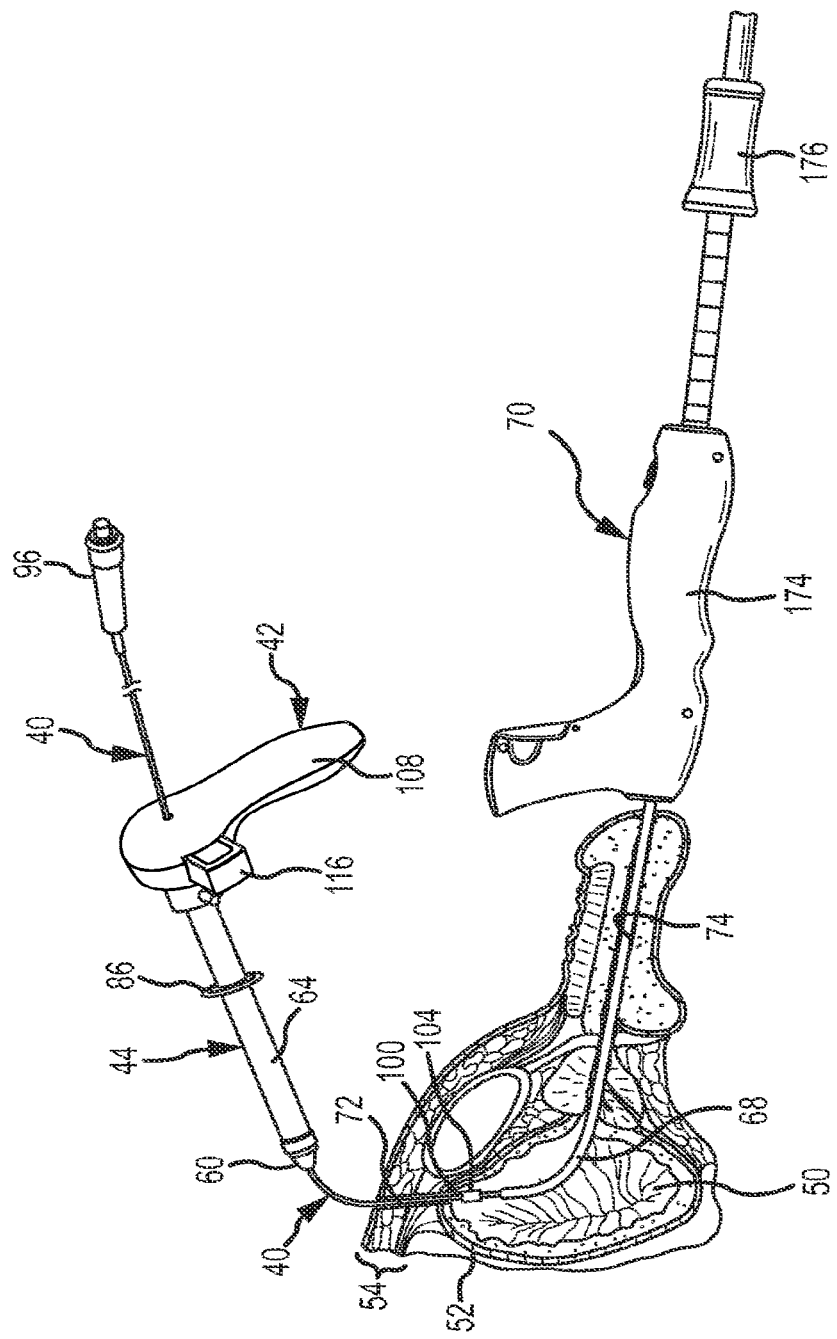
Figure 14:
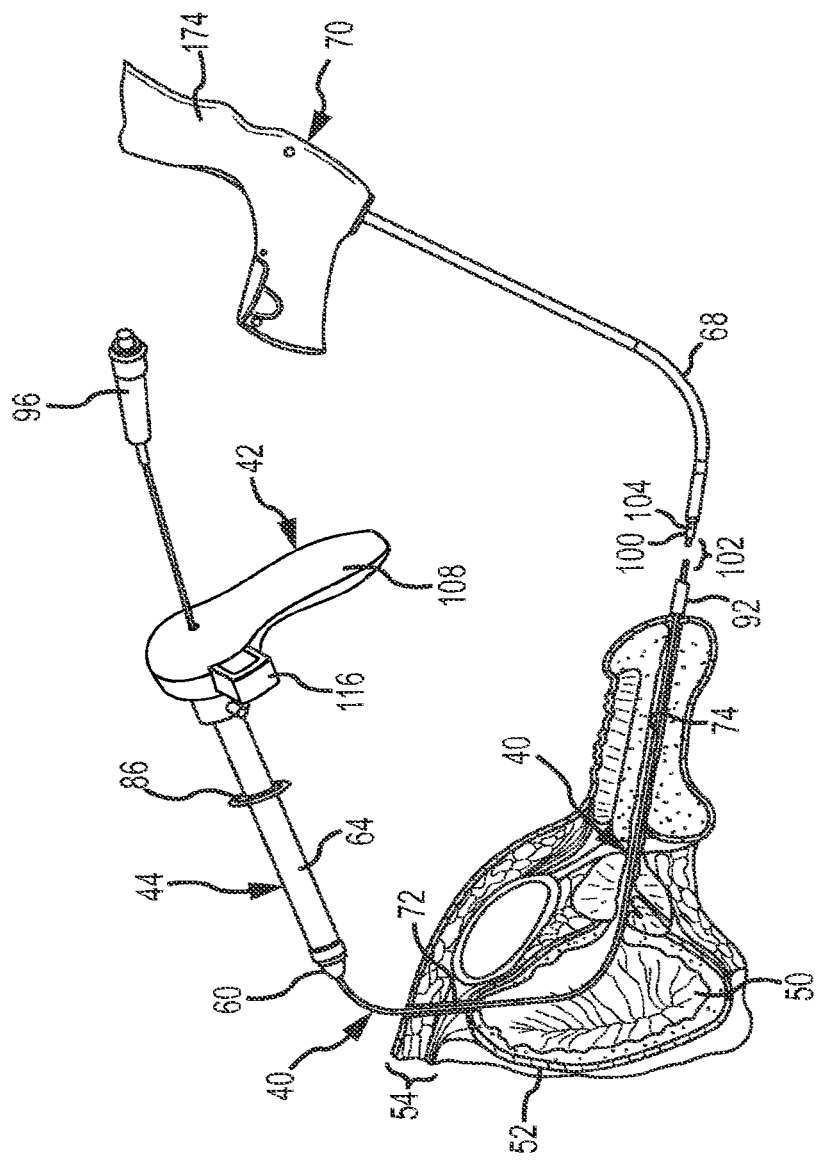
Figure 15:
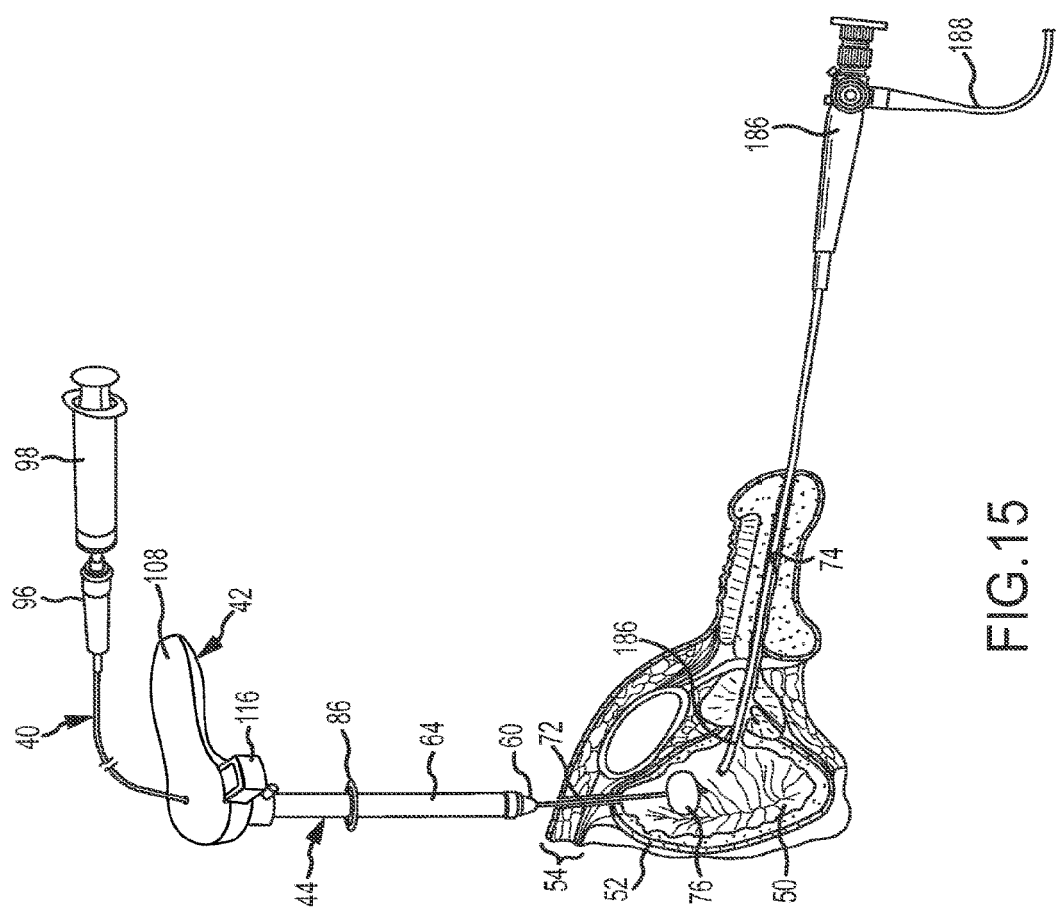
Figure 16:
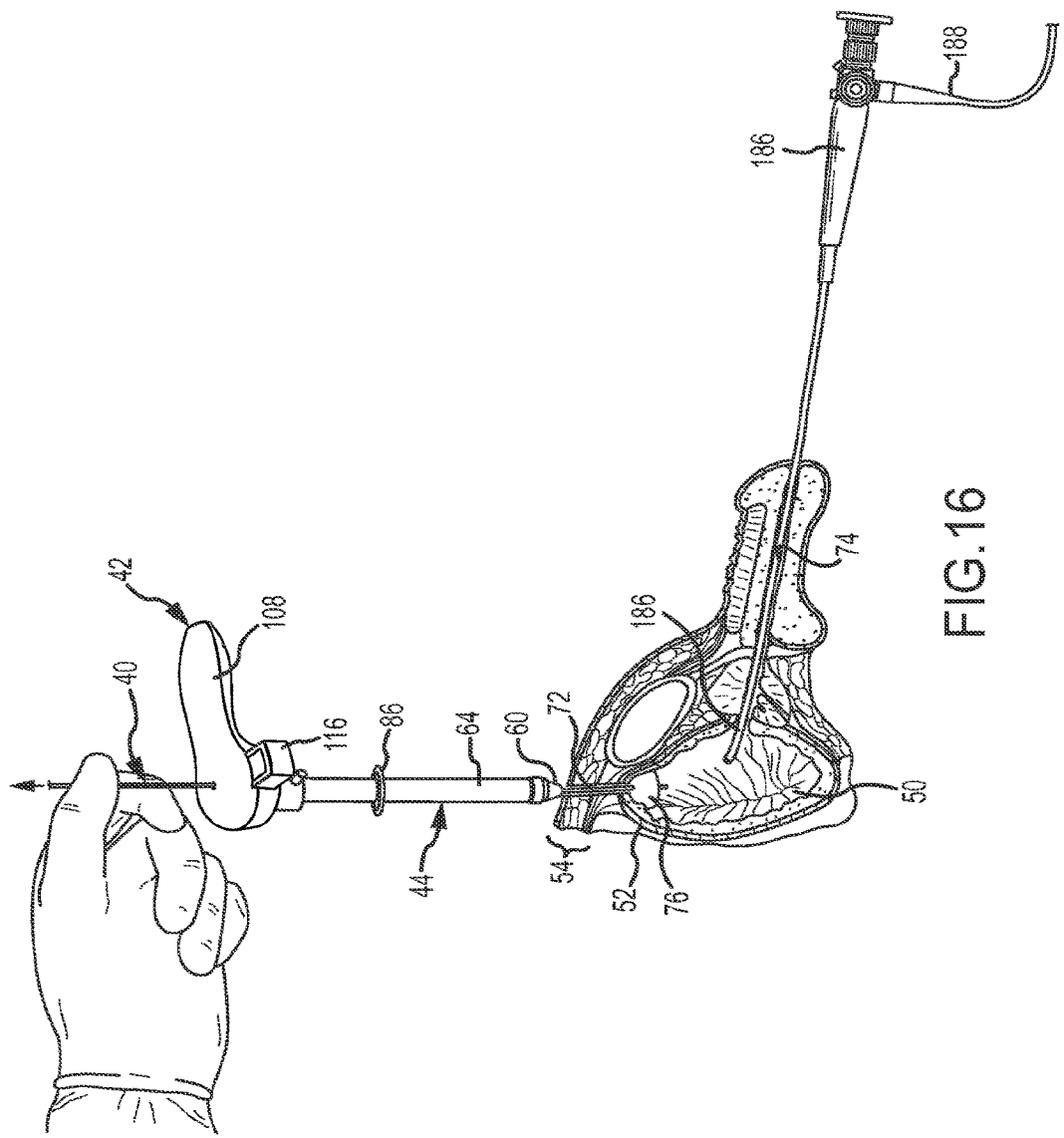

The enlarged opening 48 is formed from an initial small diameter surgical pathway 72 created by extending an advancement member 66 through the bladder wall 52 and the abdominal wall 54, as shown in FIG. 12. The advancement member 66 is extended from a sound 68 of a transurethral medical instrument 70 which has been inserted in the bladder 50 through the urethra 74. Thereafter, the forward end of the placement guide 40 is connected to the forward end of the advancement member 66, and the advancement member 66 and the sound 68 are withdrawn to pull the forward end of the placement guide 40 through the bladder 50 and urethra 74, as shown in FIGS. 13 and 14. The forward end of the placement guide 40 is then severed from the advancement member 66 (FIG. 14) and the forward end of the placement guide 40 is pulled back into the bladder 50, as shown in FIG. 15. A placement balloon 76 on the forward end of the placement guide 40 is then inflated in the bladder 50. The placement guide is pulled taut with tension pulling force applied at its rear end, moving the placement balloon 76 into adjacency with the bladder wall 52 to create a substantial sealing effect surrounding the small surgical pathway 72, as shown in FIG. 16.

Figure 17:
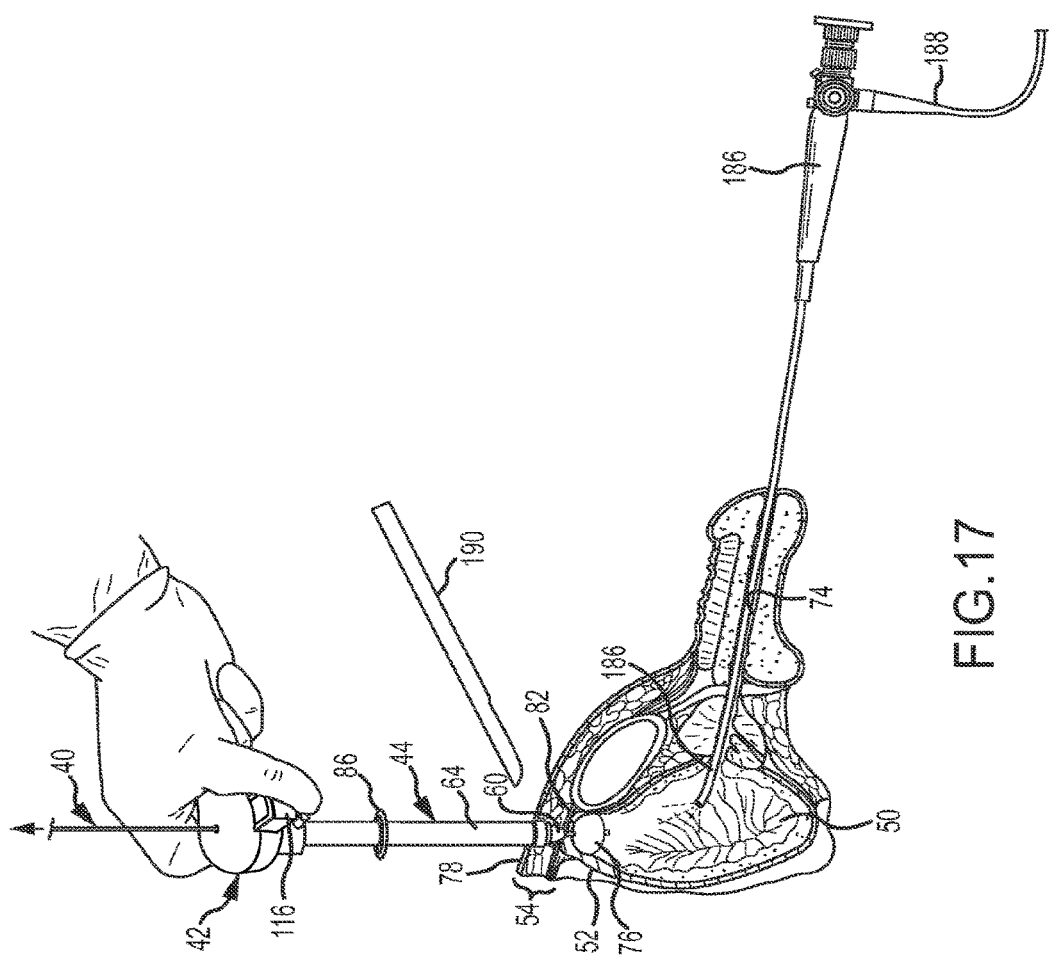

Fluid is inserted in the bladder 50 to distend the bladder wall 52 and create reactive resistance for blunt force dilation insertion movement of the forward end of the obturator 42 through the bladder wall 52, as shown in FIG. 17. The sealing effect created by the inflated placement balloon surrounding the small surgical pathway 72 prevents significant leakage of the distention fluid from the bladder 50, thereby maintaining the bladder wall in the distended condition. Small radial cuts are formed manually in the exterior skin 78 with a scalpel 79 outward from the small surgical pathway 72. Alternatively, the small radial cuts may be formed in the exterior skin 78 by momentarily extending blades 80 on the forward end of the obturator 42. The small radial cuts facilitate moving the forward end of the obturator 46 through the exterior skin 78, as shown in FIG. 17.

Figure 18:
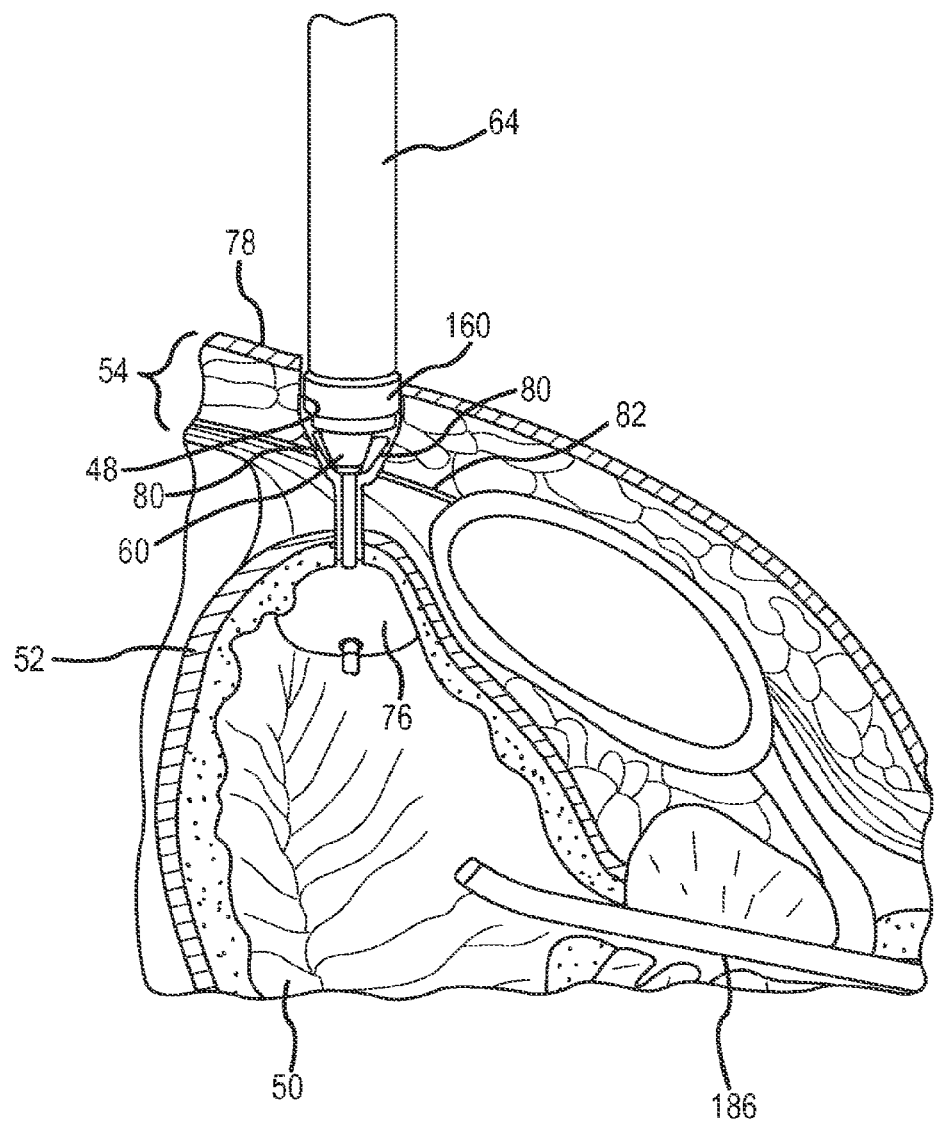

As the obturator 46 is moved into contact with an internal fascia layer 82 of the abdominal wall 54, the blades 80 on the forward end of the obturator 42 are selectively extended and retracted to cut that internal fascia layer 82, as shown in FIG. 18. The blades 80 make small cuts in the fascia layer which extend radially outward from the small diameter surgical pathway 72. The small cuts in the fascia layer 82 facilitate moving the forward end of the obturator 46 through the fascia layer with considerably reduced force, while the fluid which distends the bladder wall creates enough reactive resistance to permit effective blunt force penetration and dilation by the obturator. The small pathway 72 through the bladder wall 52 is thereby expanded into the enlarged opening 48, while the blades 80 on the forward end of the obturator are retracted.

Figure 20:
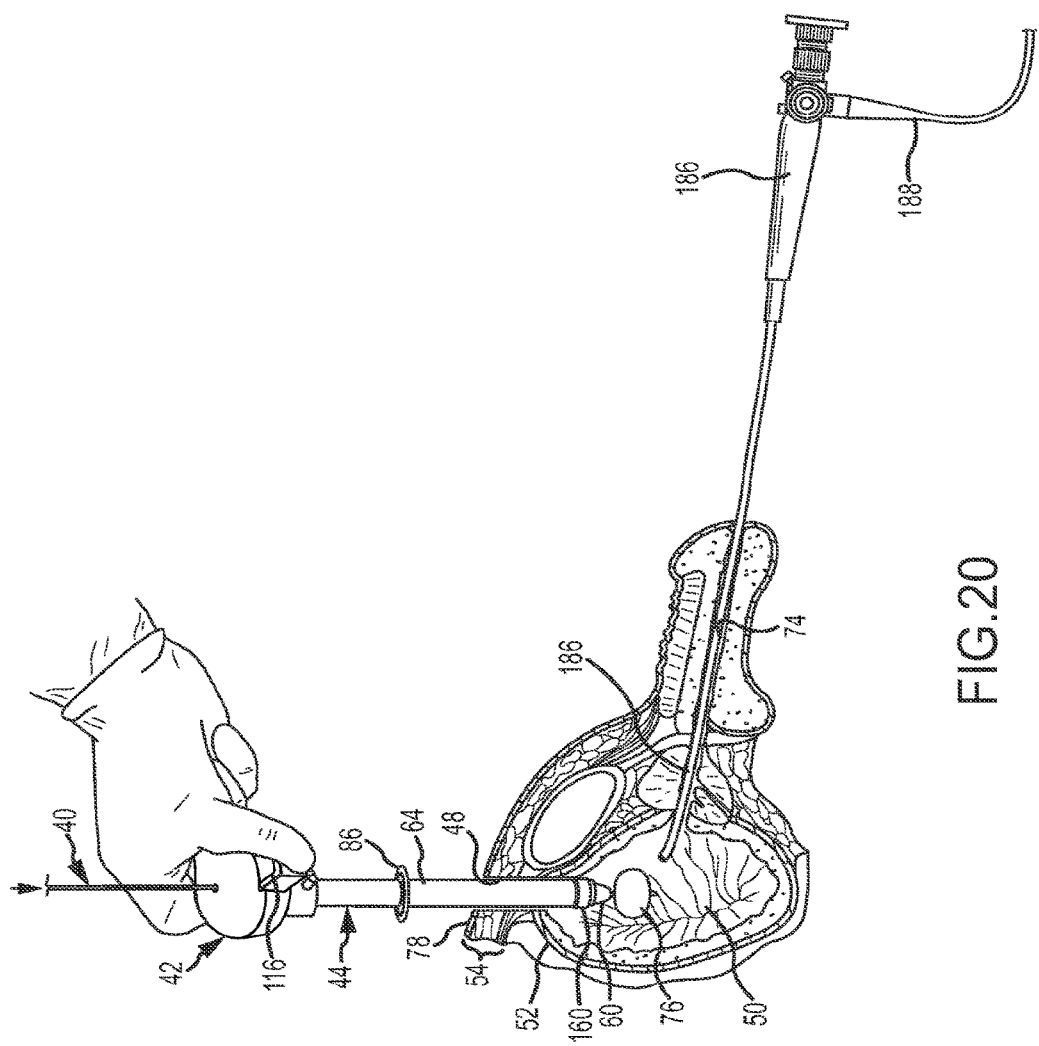
Figure 21:
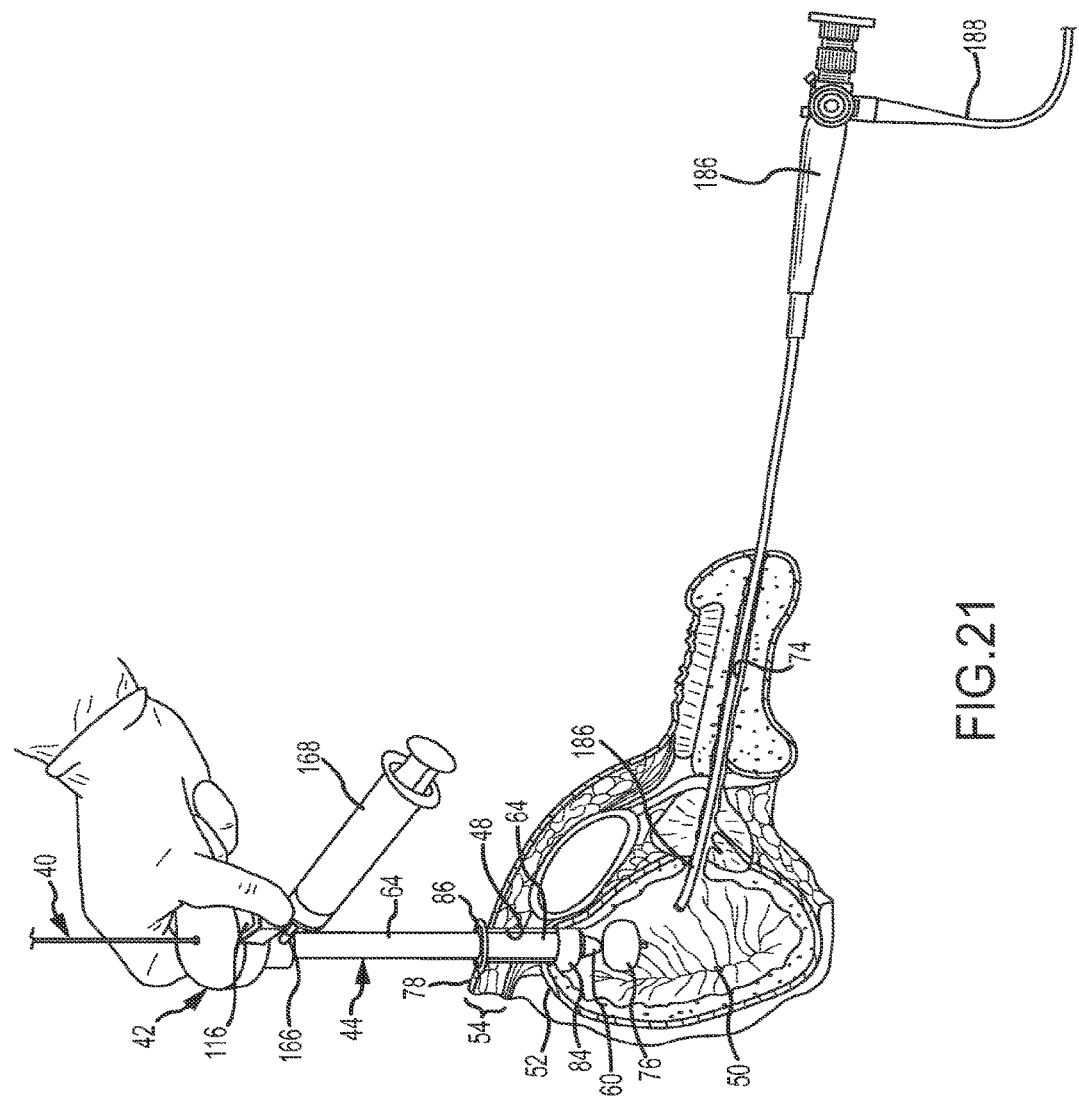

Once the forward end of the obturator 42 and cannula 44 are within the bladder 50, a stabilization balloon 84 on the forward end of the cannula 44 is inflated, as shown in FIG. 20. The apparatus 46 is then in the condition shown in FIG. 3. The inflated stabilization balloon 84 is then moved upward firmly against the bladder wall 52, as shown in FIG. 21. A retainer, such as a retention ring 86 is moved down along the conduit 64 of the cannula 44 to contact the exterior skin 78 of the abdominal wall 54 and stabilize the cannula in its use position in the enlarged opening 48. An alternative retainer, such as a retention balloon 87 on the cannula 44' shown in FIG. 9B, is inflated to apply radial force against the more rigid external skin 78 and internal fascia layer 82 of the abdominal wall 54 to assist in stabilizing the balloon in its use position.

Figure 22:
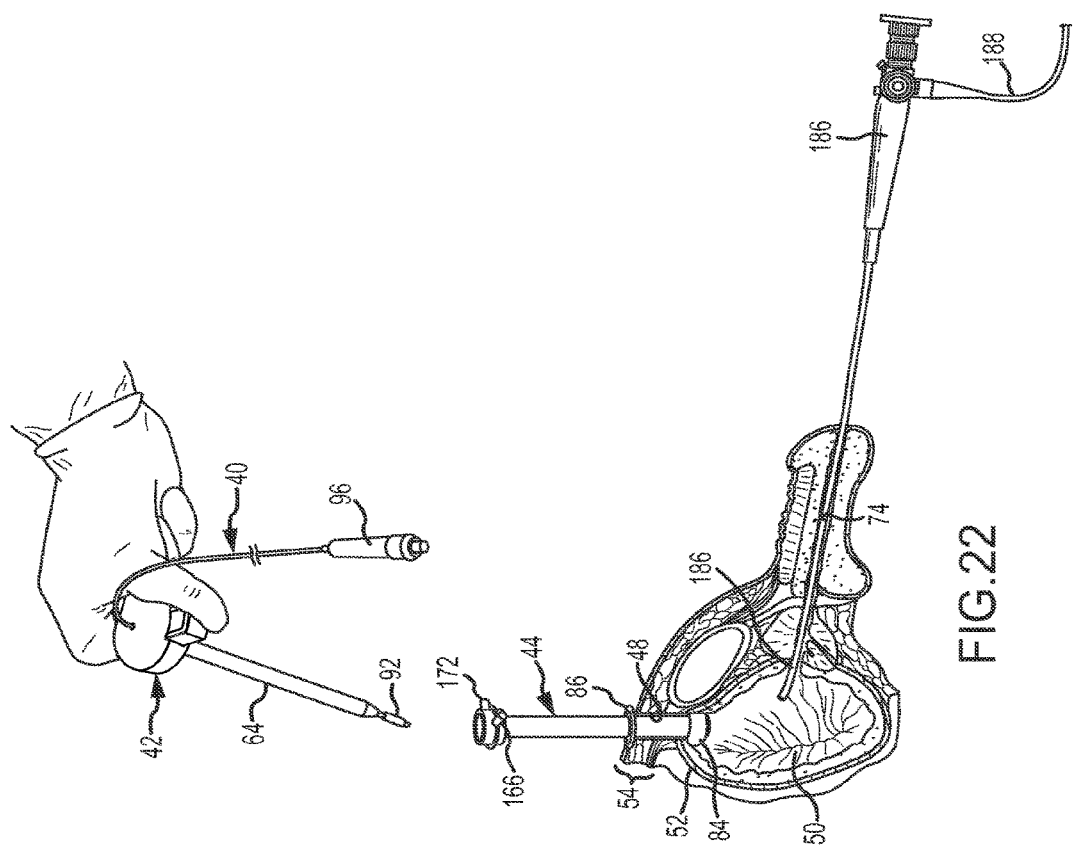
Figure 23:
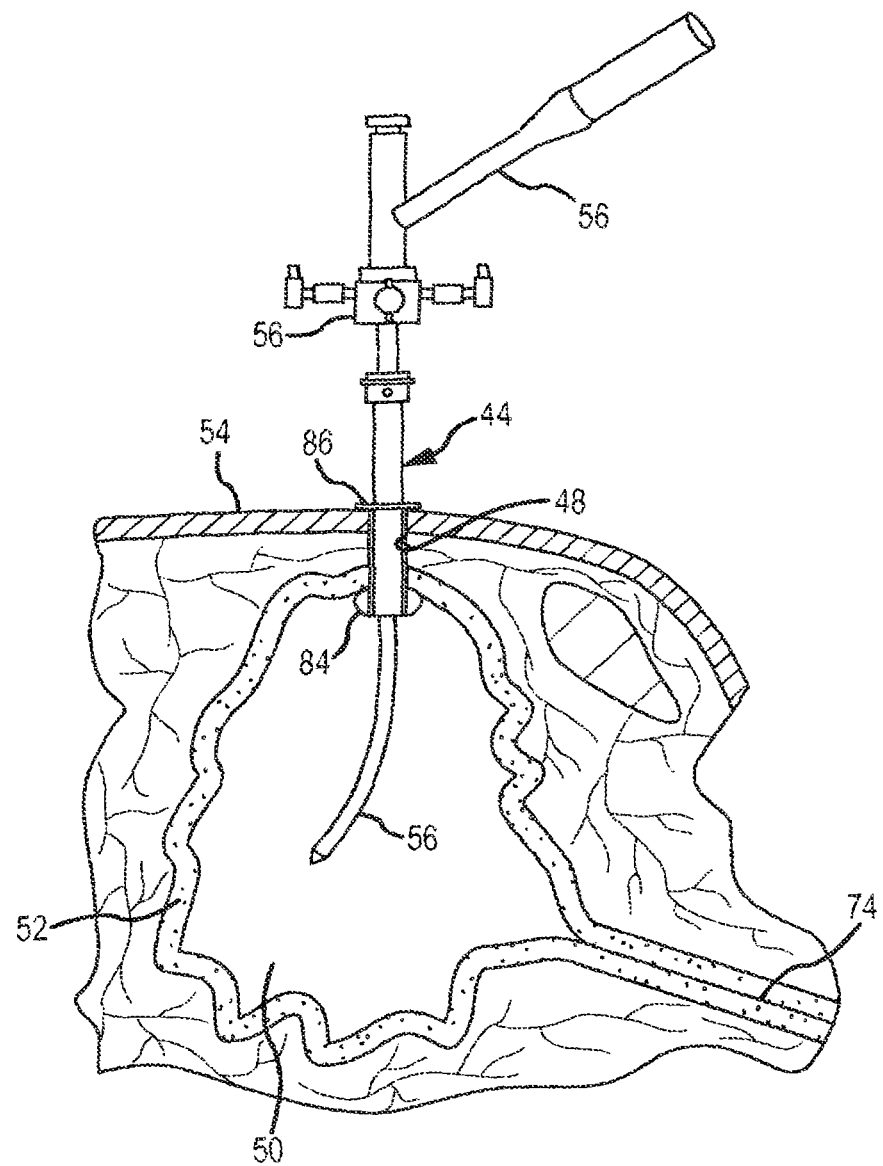

Thereafter, as shown in FIG. 22, the placement balloon 76 on the placement guide 40 is deflated, the obturator 42 is disconnected from the cannula 44, and the obturator 42 and the placement guide 44 are withdrawn from the central channel 62 of the cannula 44. The cannula 44 is left in its use position, retained against the bladder wall 52 by the inflated stabilization balloon 84 and retained against the exterior skin 78 by the retention ring 86 or retained radially against the abdominal wall 54 by the expanded retention balloon 87 (FIG. 9B), ready for medical instruments 56 to be inserted through the central channel 62 of the cannula 44 into the bladder 50, as shown in FIG. 23.

More details of the apparatus 46 (FIGS. 1-9B) and the method of placing the cannula 44 (FIGS. 10-22) are described below.

The placement guide 40 is shown in greater detail in FIGS. 4A, 4B and 4C. The placement guide 40 is formed by an elongated flexible guide tube 88. A lumen 90 extends through the guide tube 88. The placement balloon 76 on the forward end of the guide tube 88 is formed by a thin expandable membrane 92 which is sealed circumferentially to exterior of the tube 88 in two spaced part locations. A hole 94 is formed from the lumen 90 through the tube 88 at a location between the two locations where the membrane 92 is sealed to the exterior of the tube 88. The hole 94 delivers inflation fluid from within the lumen 90 into the volume on the outside of the tube 88 surrounded by the membrane 92. The fluid fills this volume and expands the membrane 92 to inflate the balloon 76.

A conventional inflation connector 96 is attached to a rear end of the tube 88, as shown in FIG. 4B. The inflation connector 96 connects to a conventional syringe 98 (FIG. 15). Fluid such as air or liquid is delivered from the syringe 98 through the inflation connector 96 and is conducted through the lumen 90 to the hole 94, where that fluid enters the volume encompassed by the membrane 92 and expands the membrane to inflate the balloon 76. Although not shown, the inflation connector 96 includes a check valve to prevent the unintended backflow of fluid from the inflated placement balloon 76, until the check valve is opened to allow the placement balloon 76 to deflate.

A mechanical connector 100 is attached to the forward end of the tube 88, as shown in FIG. 4C. A volume 102 within the lumen 90 adjacent to the mechanical connector 100 is completely closed off, such as by introducing a hardening filler material into that volume 102, after the mechanical connector 100 has been attached to the forward end of the tube 88, such as with an adhesive. Sealing off the forward end of the tube 88 in the volume 102 confines the fluid inserted within the lumen 90 and forces that fluid through the hole 94 to expand the membrane 92 into the placement balloon 76.

The mechanical connector 100 is a conventional connector, such as a bayonet connector. The connector 100 is mechanically connectable to a complementary mechanical connector 104 located on the forward end of the advancement member 66 (FIG. 12). Connecting the mechanical connectors 100 and 104 attaches the forward end of the placement guide 40 to the forward end of the advancement member 66, thereby permitting the forward end of the placement guide 40 to be pulled through the small surgical pathway 72 (FIG. 13) and then through the urethra 74 (FIG. 14).

Once the forward end of the placement guide 40 is outside of the urethra (FIG. 14), the guide tube 88 is severed midway between the ends of the sealed volume 102. Severing the tube 88 through the sealed volume 102 is accomplished with a scalpel, scissors or other cutting device. Severing the guide tube at a middle location of the sealed volume 102 maintains the lumen 90 in a sealed condition at the forward end of the tube 88, thereby permitting the balloon 76 to be inflated as described, even though the mechanical connector 100 has been removed. Removing the connector 100 by severing it from the forward end of the placement guide 40 eliminates irritation to the urethra 74 that might be caused by the connector 100 when the forward end of the placement guide 40 is pulled back through the urethra 74 to locate the balloon 76 in the bladder 50 (FIG. 15).

As shown in FIGS. 1-3 and 5, the obturator 42 includes a housing 106 located at a rear end of the obturator. The housing 106 includes a handle 108 that is grasped by the hand of a user. The cylindrical obturator shaft 60 connects to the housing 106, and extends to the forward end of the obturator 42 shown in FIGS. 6A-6D. The center passage 58 which receives the placement guide 40 extends through the housing 108 and along the obturator shaft 60.

The center passage 58 is defined in major part by a hollow actuation member or tube 110 which is positioned to move axially in a coaxial relationship with the obturator shaft 60. The open center 111 of the actuation tube 110 extends the center passage 58 from the housing 106 to the forward end of the obturator 42. The placement guide 40 extends through the open center 111 of the actuation tube 110 and completely through the obturator 42. Movement of the actuation tube 110, as described below, is not impeded by the placement guide located in the open center 111 of the actuation tube 110.

The blades 80 (three are shown) are connected to the forward end of the actuation tube 110 by welding, for example. A trigger mechanism 112 interacts with the rear end of the actuation tube 110 and causes the actuation tube 110 to move axially within the obturator shaft 60. When the trigger mechanism 112 is selectively actuated, the actuation tube 110 moves in the forward axial direction to extend blades 80 from the forward end of the obturator shaft 60. Thereafter, the actuation tube 110 moves in the rearward axial direction to retract the blades from projecting out of the forward end of the obturator shaft 60.

Figure 19:
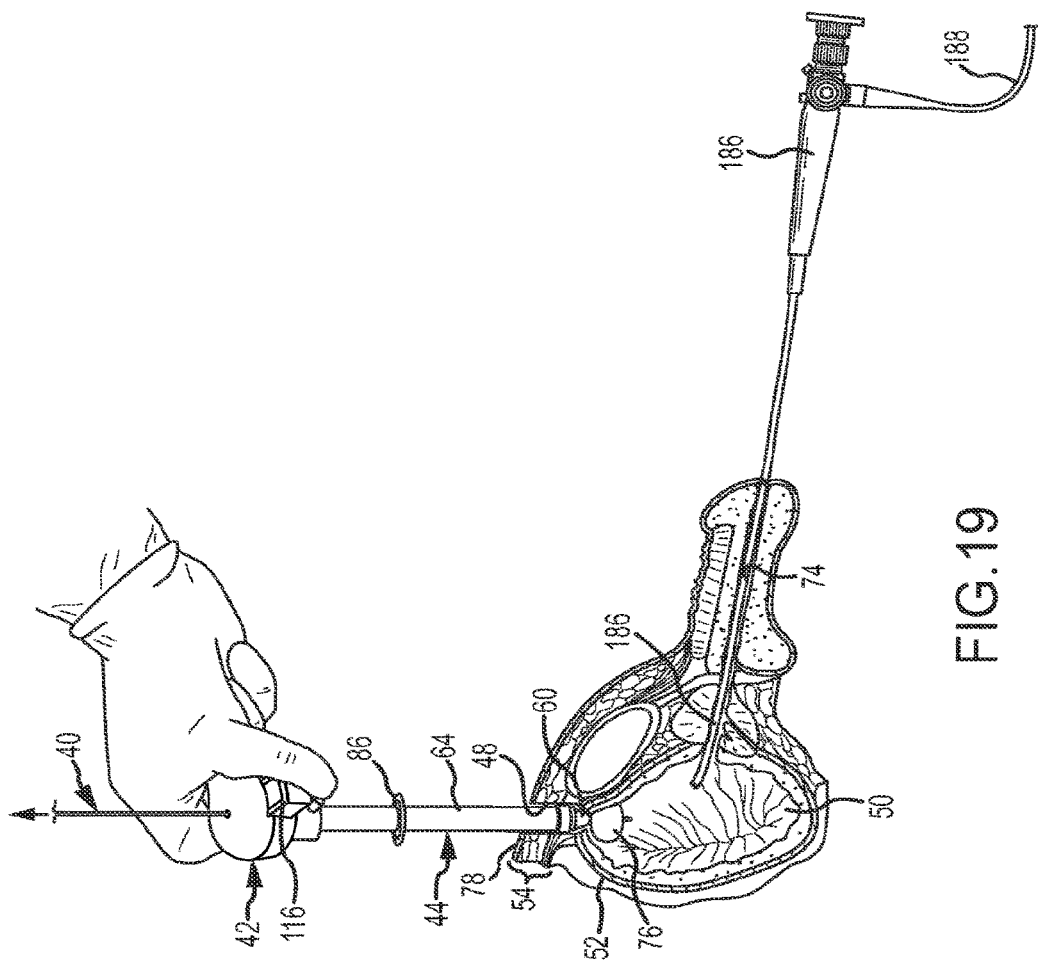

Each blade 80 moves in a track 114 formed within the forward end of the obturator shaft 60, as shown in FIGS. 6A-6D. The forward end of the obturator shaft 60 has a tapered, flared or frustoconical-like configuration with flat surfaces adjoining the tracks 114. When extended, the blades 80 project outward from the tapered forward end configuration to cut through the internal fascia layer 82 of the abdominal wall 54 (FIG. 18). In their extended position, the blades 80 extend outward to a distance no greater than the width or diameter of the conduit 64 of the cannula 44. After cutting the fascia layer, the blades 80 are retracted to a position where they do not protrude from the forward end of the obturator shaft 60. With the blades retracted, the frustoconical configuration of the forward end of the obturator shaft 60 facilitates blunt force dilation of the bladder wall 52 (FIG. 19).

Figure 5:
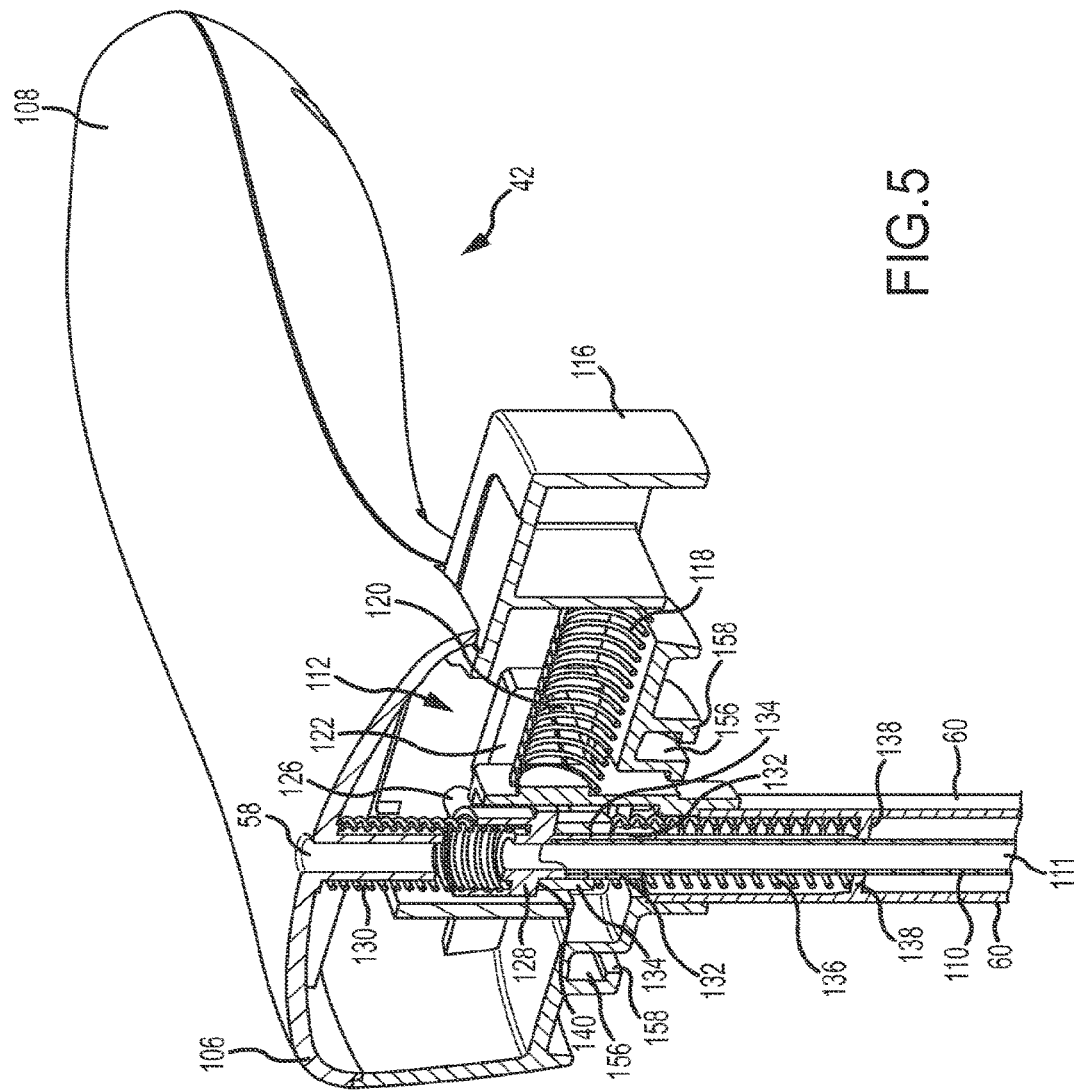
FIG. 5 is a perspective and transverse section view of a housing and rear end of the obturator shown in FIGS. 1-3.
Figure 6A:
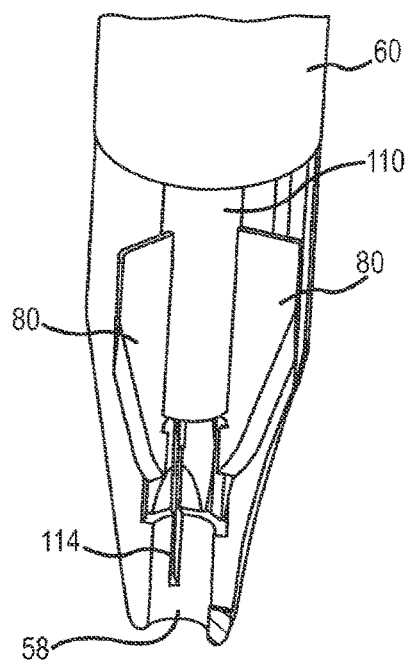
FIGS. 6A, 6B, 6C and 6D are views of a forward end of the obturator shown in FIGS. 1-3 and 5. Specifically.
Figure 6B:
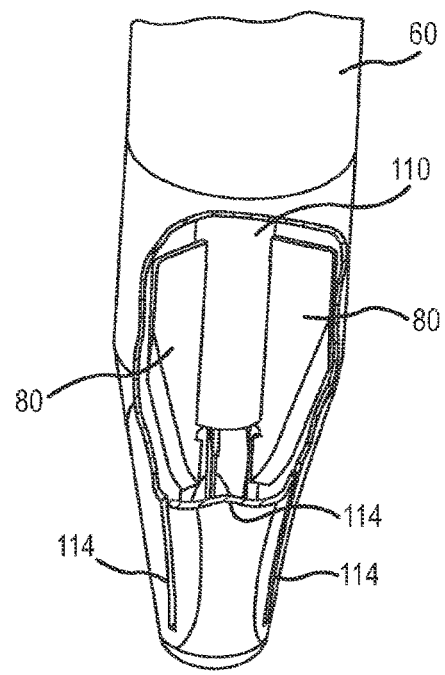
Figure 6C:
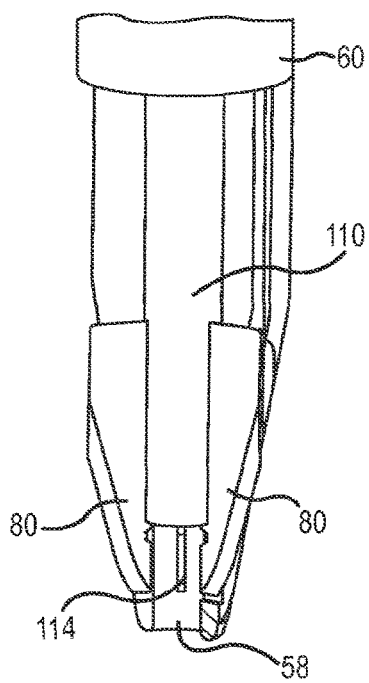
Figure 6D:
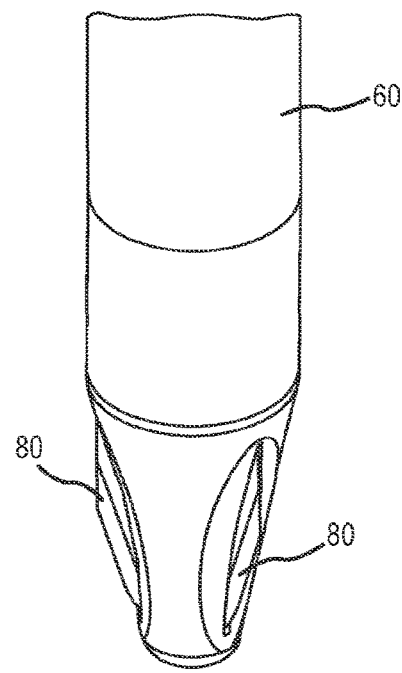

The trigger mechanism 112 is located within the upper housing 106, as shown in FIGS. 5 and 7. The trigger mechanism 112 includes an actuator button 116 which the user depresses toward the center of the housing 106, with movement preferably imparted from the thumb while the fingers of the hand grasp the handle 108. The actuator button 116 extends the blades 80 from the forward end of the obturator shaft 60 (FIGS. 6C and 6D). The actuator button 116 returns to the outward extended position (FIG. 5) when the blades retract into the forward end of the obturator shaft 60 (FIGS. 6A and 6B). A compressed button return spring 118 assists in moving the actuator button 116 out from its depressed position within the housing 106 to its extended position shown in FIG. 5.

A ramp structure 120 and a support structure 122 (FIG. 7) are part of the actuator button 116. The ramp structure 120 and the support structure 122 move transversely inward and outward within the housing 106 when the actuator button 116 is moved to the depressed position and then returned to the extended position, respectively. A follower such as a pin 124 interacts with the ramp structure 120, and another follower such as a pin 126 interacts with the support structure 122. The pin 124 moves along the top (as shown) surface of the ramp structure 120 when the actuator button 116 is moved to the depressed position to extend the blades 80 from the forward end of the obturator shaft 60. The pin 124 moves along the bottom (as shown) surface of the ramp structure 120 and the pin 126 moves along the upper (as shown) surface of the support structure 120 when the actuator button 116 returns from the depressed position to the extended position to retract the blades 80.

The pin 126 is connected to a hub 128, and the hub 128 is rigidly connected to the rear end of the actuation tube 110. Connected in this manner, the pin 126 moves vertically (as shown) in conjunction with the axial movement of actuation tube 110. The pin 126 extends transversely with respect to the actuation tube 110 to engage the upper surface (as shown) of the support structure 120 during portions of the depressed and extended movement of the actuator button 116.

An activation spring 130 extends vertically between the hub 128 and an inside surface of the housing 106. The activation spring 130 biases the hub 128 downward (as shown) toward the forward end of the obturator shaft 60. The bias on the hub 128 from the activation spring 130 supplies force to drive the actuation tube 110 toward the forward end of the obturator shaft when the actuation button 116 is depressed into the housing 106.

The hub 128 includes a sleeve 132 which surrounds the exterior surface of the actuation tube 110 and extends downward toward the forward end of the obturator shaft 60. A collar 134 is movably positioned concentrically over the sleeve 132 and moves axially along the sleeve 132. The pin 124 is connected to the collar 134. Connected in this manner, the pin 124 moves vertically in conjunction with the axial movement of collar 134 along the sleeve 132. The pin 124 extends transversely with respect to the collar 134 to engage both the top and the bottom (as shown) surfaces of the ramp structure 120, when the actuation button 116 is depressed into the housing 106 and then returns from the depressed position to be extended position.

A return spring 136 surrounds the actuation tube 110 and extends vertically between the collar 134 and an annular retaining ridge 138 formed within the interior of the obturator shaft 60. The return spring 136 biases the collar 134 upward (as shown) toward the rear end of the obturator 42. The bias on the collar 134 from the return spring 136 supplies force to move the actuation tube 110 upward (as shown) toward the rear end of the obturator when the actuation button 116 moves from the depressed position to the extended position.

The collar 134 abuts a shoulder 140 of the sleeve 132 in response to upward (as shown) bias force from the return spring 136. Force from the return spring 136 is thereby transferred from the collar 134 to the hub 128 to move the actuation tube 110 toward the rear end of the obturator. Movement of the actuation tube 110 toward the rear end of the obturator retracts the blades 80 from their extended position (FIGS. 6A and 6B).

The interaction of the pins 124 and 126 with the ramp structure 120 and the support structure 122, respectively, cause the blades 80 to extend (FIGS. 6C and 6D) and to retract (FIGS. 6A and 6B), when the actuator button 116 is depressed and then extended, respectively. The interaction of the pins 124 and 126 with the ramp structure 120 and the support structure 122 move the collar 134 and the hub 128 vertically (as shown), thereby moving the actuation tube 110 vertically to extend and retract the blades 80. This interaction is described in connection with FIGS. 8A-8I and FIGS. 5 and 7. As shown in FIGS. 8A-8I, the ramp structure 120 and the support structure 122 move horizontally relative to the horizontally-stationary pins 124 and 126.

Figure 8A:
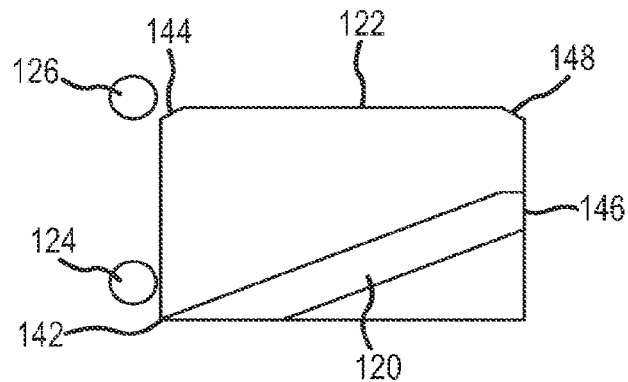
FIGS. 8A-8I are schematic illustrations of the operation of a trigger mechanism shown in FIGS. 5 and 7 which cause the blades to extend and retract as shown in FIGS. 6A-6D.

FIG. 8A depicts the normal condition where the actuator button 116 is in the extended position. In this position, the pins 124 and 126 do not contact either the ramp structure 120 or the support structure 122. The pins 124 and 126 are spaced slightly to the right (as shown) beyond the beginning ends 142 and 144 of the ramp structure 120 and the support structure 122, respectively. With the pins 124 and 126 in this position, the hub 128 and the collar 134 are biased by the blade actuating spring 130 and the return spring 136, respectively (FIGS. 5 and 7) to locate the blades in their retracted position (FIGS. 6A and 6B).

Figure 8B:
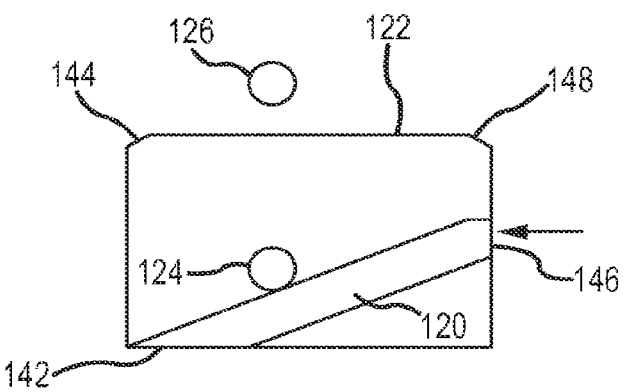

As the actuator button 116 starts depression movement, as shown in FIG. 8B, the upper surface of the ramp structure 120 at its beginning end 142 contacts the pin 124, and the movement of the ramp structure 120 begins lifting the pin 124. Because the pin 124 is connected to the collar 134 and the collar 134 contacts the hub 128 at the shoulder 140 as a result of the bias force from the return spring 136, (FIGS. 5 and 7), the movement of the pin 124 along the upper surface of the ramp structure 120 lifts the actuation tube 110 by moving it toward the rear end of the obturator 42. The pin 126 moves above the upper surface of the support structure 122, because the hub 128 and the pin 126 are lifted by the upward movement of the collar 134 caused by the pin 124 moving along the upper (as shown) surface of the ramp structure 120.

Figure 8C:
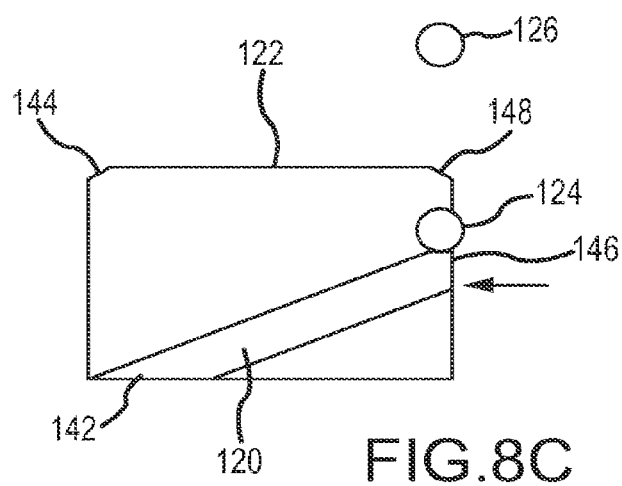

The upward movement of the collar 134, hub 128 and actuation tube 110 continues as the pin 124 continues to move upward along the upper surface of the ramp structure 120, until reaching the terminal end 146 of the ramp structure 120 as shown in FIG. 8C. In this position, the maximum amount of upward movement has occurred. The activation spring 130 (FIGS. 5 and 7) is maximally compressed between the hub 128 and the housing 106 due to the reduced distance between the hub 128 and the housing 106. At this position, the blade actuating spring 130 exerts its maximum amount of downward force on the hub 128.

Figure 8D:
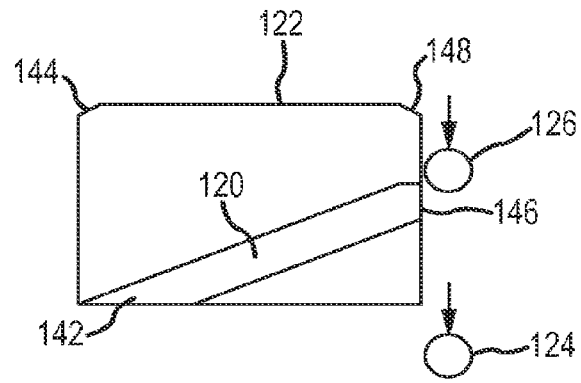

Continued depression movement of the actuator button 116 moves the terminal ends 146 and 148 of the ramp and support structures 120 and 122 beyond the pins 124 and 126, respectively, as shown in FIG. 8D. Because the terminal ends 146 and 148 of the ramp and support structures 120 and 122 are now spaced slightly to the right (as shown) from the pins 124 and 126, the force from the compressed activation spring 130 pushes downward on the hub 128 causing the actuation tube 120 to move impulsively downward (as shown) toward the front end of the obturator 42. The downward movement of the actuation tube 120 moves the blades 80 to their extended position (FIGS. 6C and 6D). In this manner, the force from the activation spring 130 provides a driving force for quickly extending the blades. The force from the compressed activation spring 130 drives the hub 128 and the collar 134 downward to a greater extent than the normal position, as shown by comparing FIG. 8D with the normal position shown in FIG. 8A. The impulsive downward driving force from the compressed activation spring 130 is sufficient to cause the blades 80 to cut tissue, including the internal fascia layer (FIG. 18).

As the pin 124 moves along the upper surface of the ramp structure 120, the amount of compression force generated by the return spring 136 diminishes because the return spring 136 elongates. The reduced amount of upward (as shown) force from the return spring 136 also facilitates greater force delivery from the activation spring 130 in moving the actuation tube 110 downward to extend the blades 82, as represented in FIG. 8D. However, the amount of compression force generated by the return spring 136 increases as the collar 134 and hub 128 reach the bottom of the stroke, as shown in FIG. 8D. The return spring 136 thereafter pushes the collar 134 and hub 128 upward (as shown). After transitory movements have ceased, the pins 124 and 126 return to their normal position as shown in FIGS. 8E and 8A.

Figure 8E:
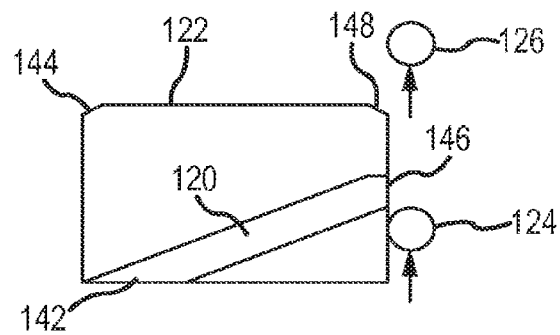

In the normal position shown in FIG. 8E, the terminal ends 146 and 148 of the ramp structure 120 and the support structure 122 are located to the left of the pins 124 and 126. In this position, the actuator button 116 is at a position of maximum depression. Thereafter, the button return spring 118 starts to move the actuator button 116 from its position of maximum depression toward its position of maximum extension.

Figure 8F:
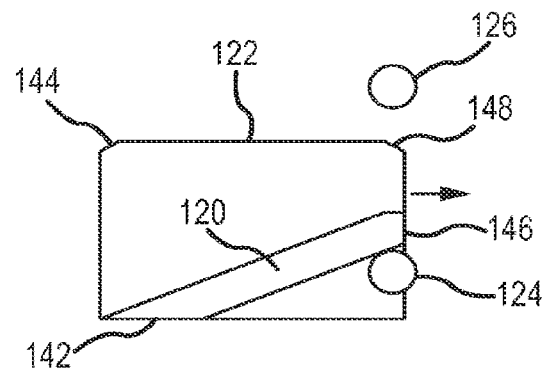

The movement of the actuator button 116 from its position of maximum depression causes the pins 124 and 126 to encounter the terminal ends 146 and 148 of the ramp structure 120 and the support structure 122, respectively. The pin 124 encounters the lower surface of the ramp structure 120, and the pin 126 encounters the upper surface of the support structure 122, as shown in FIG. 8F.

Figure 8G:
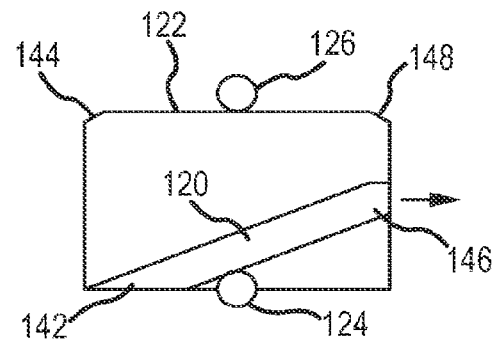

Continued movement of the actuator button 116 toward its extended position causes the pin 124 to continue moving downward along the lower surface of the ramp structure 120, as shown in FIG. 8G. The collar 134 moves downward along the sleeve 132 against the compression force of the button return spring 118. The pin 126 contacts the upper horizontal surface of the support structure 122 and stays vertically stationary as the support structure 122 moves horizontally. The support structure 122 thereby holds the pin 126 and the hub 128 connected to the actuation tube 100 in the upper position, preventing the blades 80 from extending while actuator button 116 moves from the depressed position to the extended position.

The pins 124 and 126 continue to separate from one another with continued return movement of the actuator button 116 toward the extended position. The pins 124 and 126 separate because the collar 134 moves downward (as shown) along the sleeve 132 and compresses the return spring 136. The activation spring 130 biases of the hub 128 downward (as shown) causing the pin 126 to slide along the upper horizontal surface of the support structure 122.

Figure 8H:
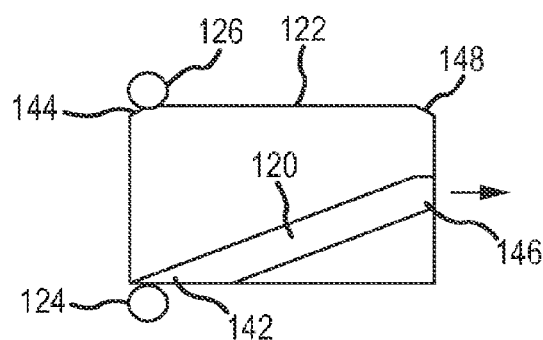

As the movement of the actuator button 116 continues toward the extended position, as shown in FIG. 8H, the pins 124 and 126 reach the beginning ends 142 and 144 of the ramp structure 120 and the support structure 122, respectively. Further movement of the actuator button 116 toward the extended position causes the pin 124 to move off of the beginning end of the lower surface of the ramp structure 120 and causes the pin 126 to move off of the upper surface of the support structure 122. At this point, the pins 124 and 126 are located slightly to the left (as shown) of the ramp structure 120 and the support structure 122.

Figure 8I:
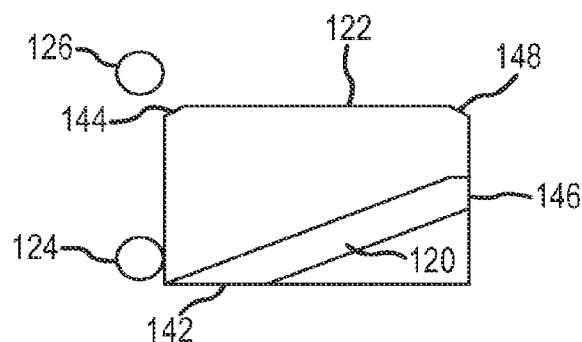

Thereafter, the compressed return spring 136 moves the collar 134 upward (as shown) to contact the shoulder 140 of the hub 128, thereby reestablishing the normal position of the pins 124 and 126 relative to the ramp and support structures 120 and 122, as shown in FIG. 8I (and also in FIGS. 8A and 8E). In the position shown in FIG. 8I, the actuator button 116 has achieved its maximum outward extension movement, and the actuator button 116 is located in a position to again be depressed, if desired.

The series of movements described in FIGS. 8F-8H are necessary to reset the pin 124 to contact the upper surface at the beginning end 142 of the ramp structure 120 when the actuator button 116 is again depressed. This reset is necessary because, after the blades 80 have been deployed momentarily by the impulse force of the activation spring 130, the pin 124 is located at a position below the upper surface of the terminal end 146 of the ramp structure 120 (FIG. 8E). In order to repeat extending the blades, pin 124 must be positioned to contact the upper surface of the ramp structure 120 at the beginning end 142 of the ramp structure 120 when the actuator button 116 is depressed.

The actuation by the trigger mechanism 112, the movement of the actuation tube 110 by the trigger mechanism 112, and the extension and retraction of the blades 80 are accomplished without interference from the placement guide 40 located within the center passage 58 of the obturator 44 and without interference from the conduit 64 of the cannula 44 which surrounds the obturator shaft 60. The open center 111 of the actuation tube 110 provides sufficient clearance from the guide tube 88 of the placement guide 42 permit the axial movement of the actuation tube 110 without impairment from the placement guide 42. The forward end of the conduit 64 of the cannula 44 terminates at a position slightly rearwardly spaced from the location where the blades 88 extend outward from the forward end of the obturator shaft 60.

The interaction of the pins 124 and 126 with the ramp structure 120 and the support structure 122 cause the blades to momentarily extend and then retract into the forward end of the obturator 42. The blades 80 are momentary extended followed immediately by retraction. The extension and retraction action occurs automatically. Manual extension and manual retraction of the blades can be achieved by modifying the ramp structure 120 and the support structure 122 to move the pin 126 downward (as shown) to extend the blades 80 in response to depression movement of the actuator button 116. With such modifications, the blades 80 are held in the extended position so long as the actuator button 116 remains depressed, and releasing the depression pressure on the actuator button allows it to move outward and retract the blades to their retracted position. Manual control over the extension and retraction of the blades may be preferred by some surgeons, as opposed to the automatic snap action actuation specifically described herein.

The cannula 44 and the obturator 42 are connected as a unit by interaction of the rear end of the conduit 64 of the cannula with the housing 106 of the obturator 42. The rear end of the cannula 44 includes a generally cylindrical annular flange structure 150. A wall 152 of the flange structure 150 has a pair of diametrically opposed fractional-turn, twist lock grooves 154 formed in the wall 152. The housing 106 of the obturator 42 includes an annular slot 156 formed in the bottom surface of the housing 106 at a position concentric with the location where the obturator shaft 60 extends from the housing 106. The annular slot 156 of the obturator 42 receives the annular flange structure 150 of the cannula, when the obturator and the cannula are locked together. Diametrically-positioned inward-protruding tabs 158 extend into the annular slot 156. The tabs 158 are aligned with the twist lock grooves 154 of the flange structure 150 of the obturator 42, when the obturator and the cannula are connected together. With the tabs 158 positioned in the grooves 154, relative rotational movement of the obturator 42 and the cannula 44 moves the tabs 158 firmly into the twist lock grooves 154 to connect the obturator 42 and the cannula 44 firmly together as a unit. Although the twist lock mechanism described above is one example of a selectively releasable connecting mechanism for connecting the obturator and the cannula together as a unit, other types of connecting mechanisms can be employed.

Figure 9A:
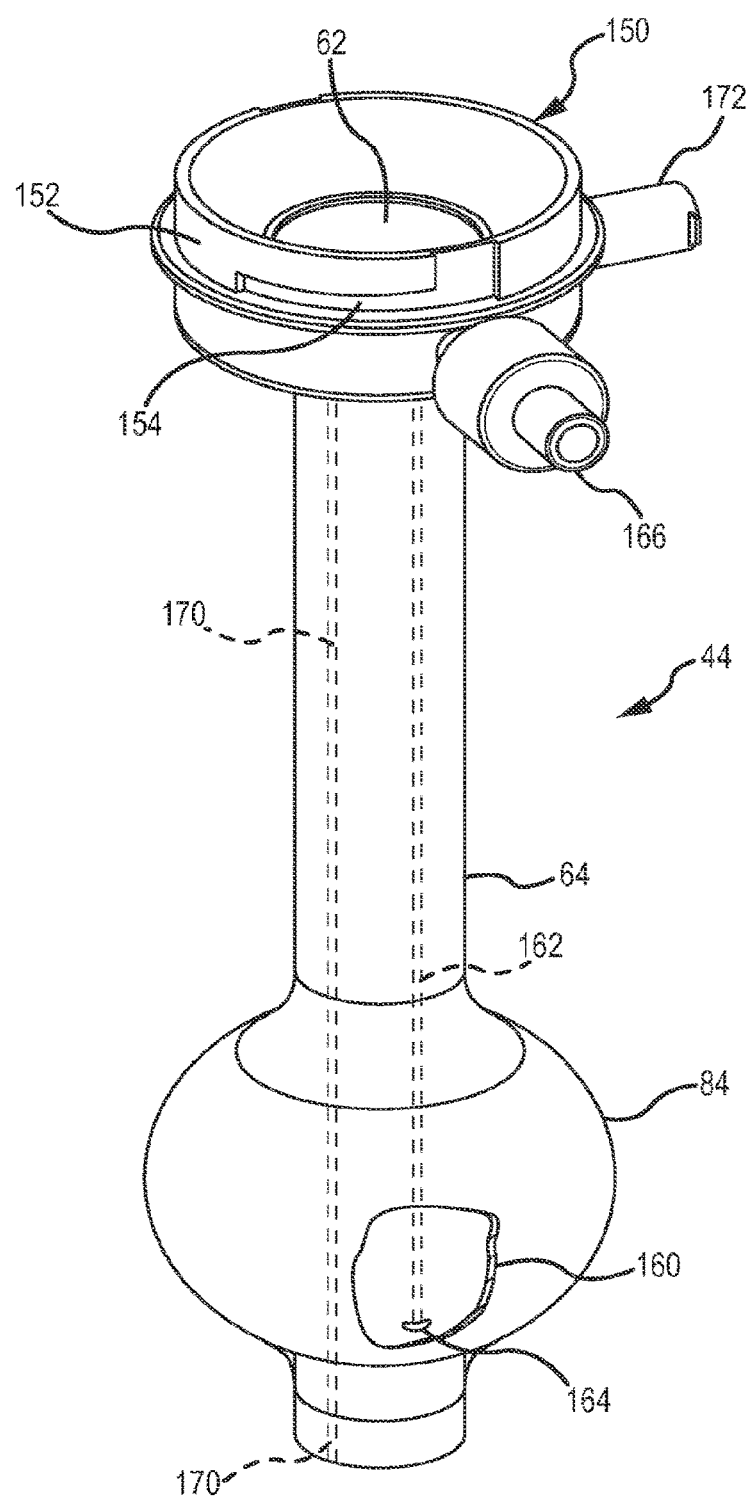
FIG. 9A is an enlarged perspective view of the cannula shown in FIGS. 1-3, with its stabilization balloon inflated as shown in FIG. 3.
Figure 9B:
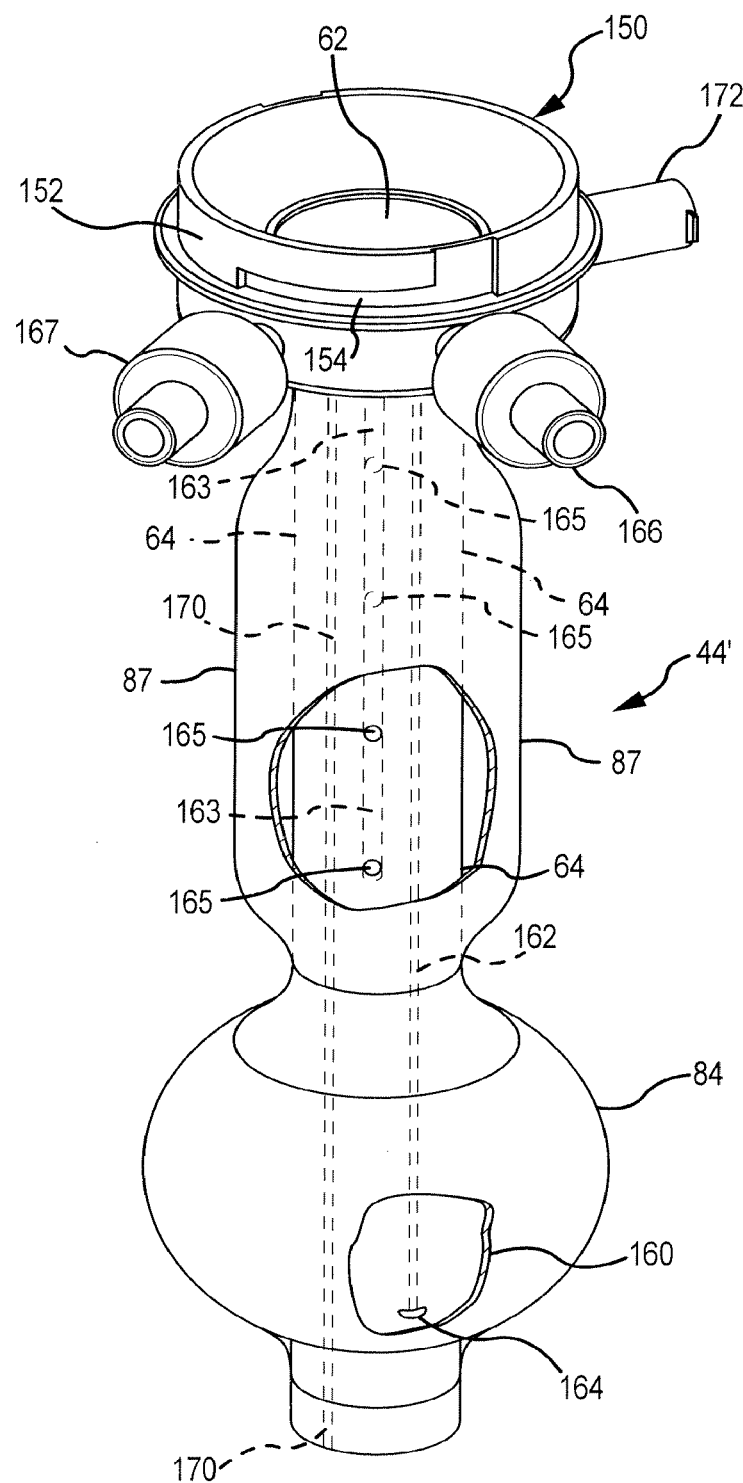
FIG. 9B is a perspective view of an alternative cannula to that shown in FIG. 9B.

The stabilization balloon 84 on the forward end of the conduit 64 of the cannula 44 is formed by a thin expandable membrane 160 which is sealed circumferentially to exterior of the conduit 64 in two spaced part locations, as shown in FIG. 9A. A fluid passageway 162 is formed within the wall of the conduit 64, and the fluid passageway 162 terminates at a hole 164. The hole 164 is positioned between the two locations where the membrane 160 is sealed to the exterior of the conduit 64. The hole 164 delivers inflation fluid from the fluid passageway 162 into the volume enclosed by the membrane 160 on the exterior of the conduit 64. The fluid fills the volume between the membrane 160 and the exterior of the conduit 64, thereby expanding the membrane 160 and forming the stabilization balloon 84.

A conventional inflation connector 166 is attached to the flange structure 150. The fluid passageway 162 communicates with the inflation connector 166. The position of the inflation connector 166 on the flange structure 150 avoids interference with the housing 106 of the obturator 42 when the obturator and the cannula are connected together. A conventional syringe 168 (FIG. 21) connects to the inflation connector 166 to deliver fluid such as air or liquid through a fluid introduction port formed by the inflation connector 166 and the fluid passageway 162 to the hole 164 to inflate the stabilization balloon 84. Although not shown, the inflation connector 166 includes a check valve to prevent the unintended backflow of fluid from the inflated stabilization balloon 84, until the check valve is opened to allow the stabilization balloon to deflate.

The cannula 44 also includes a fluid conductive passageway 170. The fluid conductive passageway 170 extends through the interior of the conduit 64 and terminates at the forward end of the conduit 64. A port 172 is connected to the flange structure 150, and the port 172 communicates with the fluid conductive passageway 170. As is typical in minimally invasive bladder surgery, it is frequently advantageous to maintain the bladder filled with liquid. The fluid conductive passageway 170 and the port 172 are used to fill the bladder with liquid by connecting a source of liquid, typically saline, to the port 172. Alternatively, the fluid conductive passageway 170 and the port 172 may be used to drain fluid from the bladder, by connecting a source of vacuum or reduced pressure to the port 172. Although not shown, multiple fluid conductive passageways 170 could be formed in the cannula to both supply fluid and remove fluid.

Although not shown, a seal is located within the interior of the conduit 64 of the cannula 44 to prevent fluid within the bladder from exiting through the central channel 62 when the obturator 42 is removed is removed from the conduit 64. The seal is a conventional item, and has the capability to mold around instruments 56 (FIG. 23) which are inserted through the central channel 62 after the cannula has been placed in its use position within the enlarged opening 48.

An alternative to the cannula 44 (FIG. 9A) is a cannula 44' shown in FIG. 9B. The cannula 44' includes essentially the same features as those of the cannula 44, except that the cannula 44' includes the expandable retention balloon 87 which is inflated only after the cannula 44' is positioned in the expanded opening 48. The retention balloon 87 is located between the stabilization balloon 84 and the flange structure 150. The retention balloon 87 is formed by a thin expandable membrane 161 which is sealed circumferentially to exterior of the conduit 64 in two spaced part locations above the stabilization balloon 84 and below the flange structure 150. A fluid passageway 163 is formed within the wall of the conduit 64, and the fluid passageway 163 communicates with a series of hole 165 formed through the wall of the conduit 64 into the fluid passageway 163 at different locations along the length of the fluid passageway 163. The holes 165 are positioned between the two locations where the membrane 161 is sealed to the exterior of the conduit 64. The holes 165 deliver inflation fluid from the fluid passageway 163 into the volume enclosed by the membrane 161 on the exterior of the conduit 64. The fluid fills the volume between the membrane 161 and the exterior of the conduit 64, thereby expanding the membrane 161 and forming the retention balloon 87.

The retention balloon 87 expands radially from the cannula 44, and such radial expansion is against the abdominal wall 54 in the enlarged opening 48 (FIGS. 19-22). Because of the relatively firm and inflexible characteristics of the exterior skin and 78 and the internal fascia layer 82, the radial expansion of the retention balloon 84 firmly positions the cannula 44 relative to the relatively firm structure of the abdominal wall, thereby stabilizing and retaining the balloon in the enlarged opening. Multiple holes 165 are formed through the conduit 64 of the cannula 44 at different locations along the length of the fluid passageway 163, to assure that fluid will flow into the interior volume between the membrane 161 and the exterior of the conduit 64 and achieve radial expansion. If only a single hole 165 from the fluid passageway 163 was used, there is a potential that contact with the relatively firm structure of the surrounding abdominal wall 54 could sufficiently block that single hole and prevent inflation of the retention balloon 87.

A conventional inflation connector 167 is attached to the flange structure 150. The fluid passageway 163 communicates with the inflation connector 167. The position of the inflation connector 167 on the flange structure 150 avoids interference with the housing 106 of the obturator 42 when the obturator and the cannula are connected together. A conventional syringe 168 (FIG. 21) connects to the inflation connector 167 to deliver fluid such as air or liquid through a fluid introduction port formed by the inflation connector 167 and the fluid passageway 163 to the holes 165 to inflate the retention balloon 87. Although not shown, the inflation connector 167 includes a check valve to prevent the unintended backflow of fluid from the inflated retention balloon 87, until the check valve is opened to allow the retention balloon to deflate.

Multiple lengths of the obturator 42 and the cannula 44 are used to accommodate patients having different thicknesses of the abdominal wall 54. For example, morbidly obese patients may require a considerably longer obturator 42 and the cannula 44 (or 44') to accomplish the procedures described below.

The series of actions or procedures involved in placing the cannula 44 in the enlarged opening 48 are described more fully below by reference to FIGS. 10-22. The anatomy of a male human is shown in FIGS. 10-23, but the same described actions are applicable with respect to female humans or other living beings.

Figure 10:
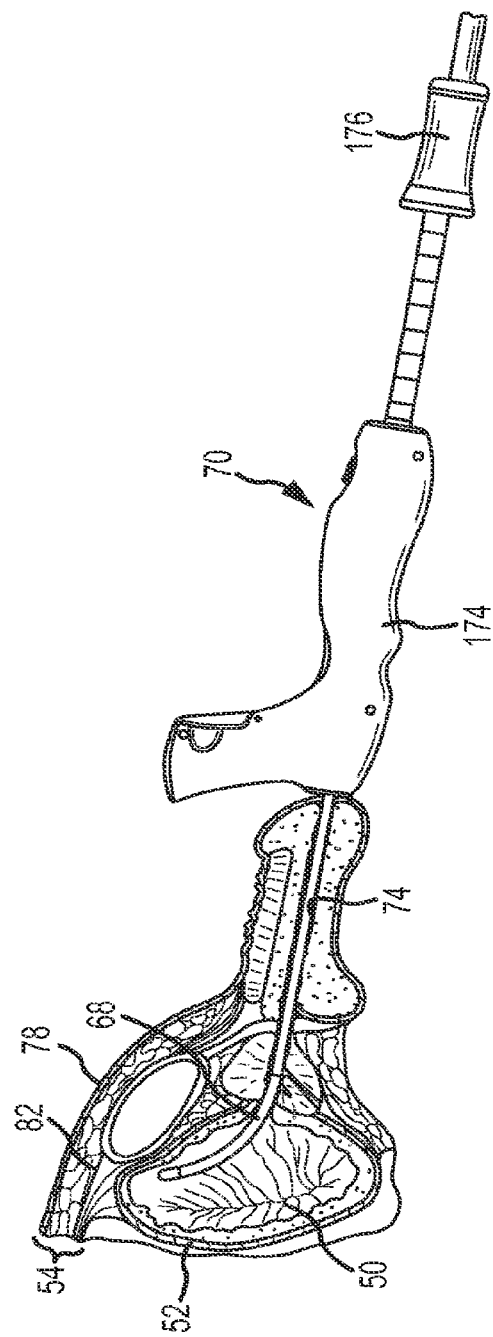
FIGS. 10-23 show a series of procedures and acts involved in enlarging an initial small surgical pathway through the bladder wall and abdominal wall into an enlarged opening in which to place the catheter, which incorporates methodology of the present invention. The anatomy of a male human is shown in cross-section in FIGS. 10-23. Each of FIGS. 10-23 is more specifically described below.
Figure 11:
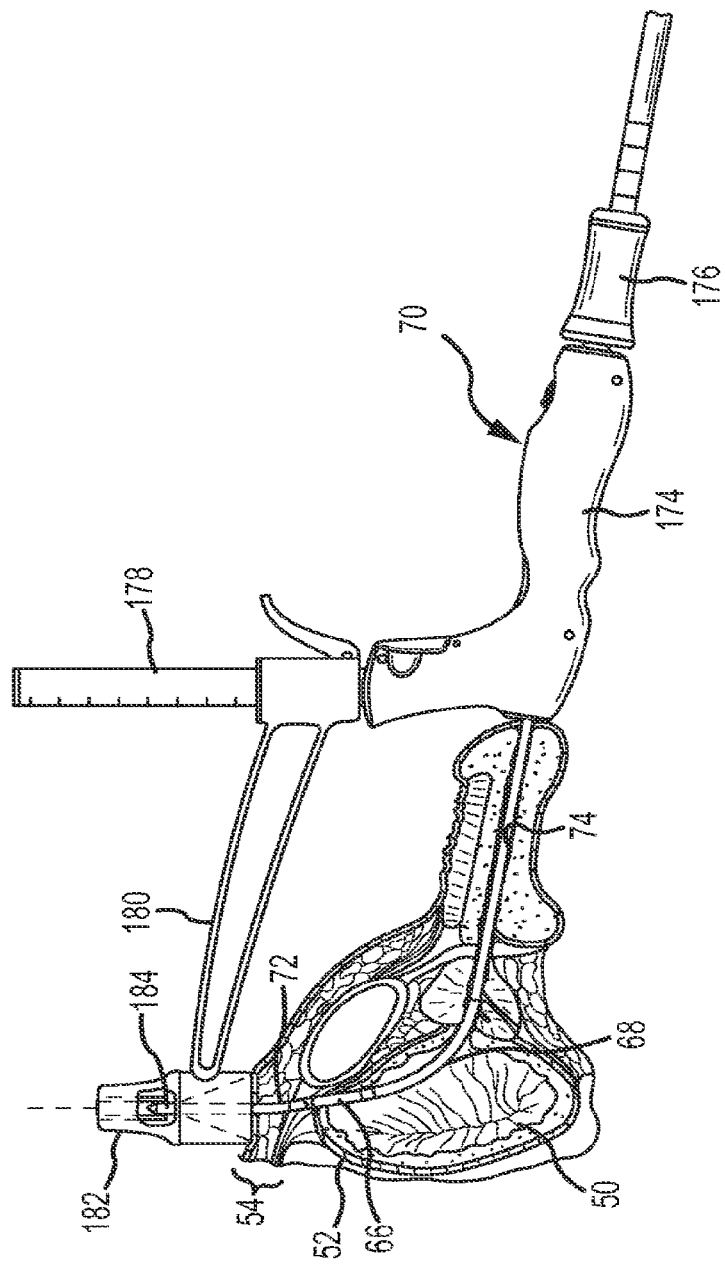

If the small surgical pathway 72 has not been previously formed, it may be formed advantageously using the procedures and transurethral medical instrument 70 described in FIGS. 10-12. The sound 68 of the transurethral medical instrument 70 is inserted through the urethra 74 until the forward end of the sound 68 is located in the bladder 50, as shown in FIG. 10. The transurethral medical instrument 70 and its use in this regard is more fully described in U.S. Pat. No. 8,118,826, which is assigned to the assignee hereof. The user manipulates the instrument 70 from a handle 174 to insert and position the sound 68. The sound 68 is essentially a tube within which the advancement member 66 is movably positioned. A knob 176 is attached to the rear end of the instrument 70 by which to extend and retract the advancement member 66 from the forward end of the sound 68 (FIGS. 11 and 12).

The forward end of the sound 68 is manipulated to contact the bladder wall 52 at a location where the small diameter surgical pathway 72 is to be formed. This location is established by forcing the forward end of the sound 68 against the bladder wall, creating a small protrusion or tenting effect at the exterior of the abdominal wall 54.

Prior to forming the small surgical pathway 72, a mast 178 is attached to the handle 174, and an arm 180 is attached to the mast 178, as shown in FIG. 11. A capture cup 182 is attached to the end of the arm 180 which is opposite from the end of the arm 180 that is connected to the mast 178. The arm 180 is moved along the mast 178 until the capture cup 182 contacts the exterior skin 78 of the abdominal wall 54. The length of the arm 180 and the orientation of the mast 178 on the handle 174 align the capture cup 182 with the path that the advancement member 66 will take when that advancement member is extended from the forward end of the sound 68.

The advancement member 66 is then advanced from the forward end of the sound 68 by forward movement of the knob 176, as shown in FIG. 11. The forward end of the advancement member 66 has a cutter 184 attached to it. The cutter 184 cuts the small surgical pathway 72 through the bladder wall 52 and the abdominal wall 54 as the advancement member 66 moves forward. The cutter 184, the mechanical connector 104 and the forward end of the advancement member 66 exit through the exterior skin 78 and move into the capture cup 182. The cutter 184 cuts into a resilient portion of the capture cup 182, thereby restraining the cutter 184 within the capture cup.

The capture cup 182 is removed from the end of the arm 180 with a twisting motion. The twisting motion disconnects the captured cutter 184 from the mechanical connector 104 on the forward end of the advancement member 66. The arm 180 and the mast 178 are thereafter removed from the handle 174. The forward end of the advancement member 66 and the mechanical connector 104 are exposed above the exterior skin 78 of the abdominal wall, as shown in FIG. 12.

Next, as understood from FIG. 13, the mechanical connector 100 (FIG. 4C) on the forward end of the placement guide 40 is connected to the mechanical connector 104 on the forward end of the advancement member 66. Previous to this, the cannula 44 has been connected to the obturator 42 by mating the tab 158 with the twist lock groove 154 (FIGS. 5 and 9). The retention ring 86 has been placed on the exterior surface of the conduit 64 of the cannula 44 (FIG. 9A), or the cannula 44' (FIG. 9B) is used as an alternative. The placement guide 40 has been inserted through the center passage 58 of the obturator 42 (FIG. 1). With the forward ends of the placement guide 40 and the advancement member 66 connected at the connectors 100 and 104, the knob 176 is moved backward to withdraw the forward end of the advancement member 66 until the mechanical connector 104 contacts the forward end of the sound 68. This action draws the forward end of the placement guide 40 through the small surgical pathway 72 and into the bladder 50 as shown in FIG. 13.

The handle 174 of the medical instrument 70 is then manipulated to withdraw the sound 68 from the urethra 74. The forward end of the placement guide 40 moves through the bladder 52 and the urethra 74 as the sound 68 is withdrawn from the urethra 74, as shown in FIG. 14. With the connectors 100 and 104 outside of the urethra 74, the placement guide 40 is disconnected from the advancement member 66 by cutting through the placement guide 40 in the sealed volume 102 (FIG. 4C). The mechanical connector 100 on the forward end of the placement guide (FIG. 4C) is separated from the remainder of the placement guide. The mechanical connector 100 is no longer available to irritate the urethra 74 when the forward end of the placement guide 40 is pulled back through their urethra 74 into the bladder 50, as shown in FIG. 15. Although the transurethral medical instrument 70s used to draw the placement guide 40 through the small surgical pathway 72 and into the bladder 50 and through the urethra 74, as shown in FIGS. 13 and 14, other types of urological devices could be used for that purpose.

The forward end of the placement guide 40 is moved through the urethra 74 and into the bladder 50 by pulling the rear end of the placement guide 40, as shown in FIG. 15. A conventional cystoscope 186 is inserted through the urethra 74 as the forward end of the placement guide 50 is withdrawn into the bladder 50. The cystoscope 186 allows the inside of the bladder 50 to be visualized. Use of the cystoscope 186 confirms that the forward end of the placement guide 40 is located within the bladder 50.

With the location of the forward end of the placement guide 40 in the bladder 50, the placement balloon 76 is inflated within the bladder 50. The syringe 98 is connected to the inflation connector 96 on the rear end of the placement guide 40, and fluid is forced through the lumen 90 of the guide tube 88 to expand the flexible membrane 92 (FIG. 4A) and inflate the placement balloon 76. Once the balloon 76 has been inflated with the syringe 98, the syringe is disconnected from the inflation connector 96. The check valve within the inflation connector 96 maintains the inflation fluid within the balloon 76 and causes it to remain inflated.

The inflated placement balloon 76 is then moved upward against the bladder wall 52 by pulling with tension force at the rear end of the placement guide 40, as shown in FIG. 16. The pulling tension force from the placement guide 40 is transferred through the expanded placement balloon 76 to contact the bladder wall 52 firmly and create a substantial sealing effect from the expanded placement balloon 76 surrounding the small surgical pathway 72. The taut force applied through the placement guide 40 and the balloon 76 also establishes and maintains alignment of the small surgical pathway 72 through both the bladder wall 52 and the abdominal wall 54, thereby preventing the incision through the flaccid bladder wall 52 from moving relative to the incision formed through the abdominal wall 54. Direct alignment of the portions of the small diameter surgical pathway 72 through the bladder wall 52 and the abdominal wall 54 facilitates enlarging the small pathway 72 into the enlarged opening 48 (FIGS. 20-23). Without the direct alignment, the flaccid bladder wall 52 may move or wrinkle and prevent the small surgical pathway 72 through the bladder wall 52 from enlargement, or may cause enlargement through the bladder wall 52 to occur in a location other than where the small surgical pathway is located.

Once the condition shown in FIG. 16 is established, fluid is introduced into the bladder 50 through the cystoscope 186. As is typical, the cystoscope 186 includes a fluid connector 188 into which fluid is delivered into the rear end of the cystoscope and conducted through an interior channel within the cystoscope to its forward end. The fluid delivered from the cystoscope 186 fills the bladder 50 and expands the flaccid bladder wall 52 to create reactive resistance to allow blunt force dilation of the bladder wall with the forward end of the obturator 42. The sealing effect from contacting the placement balloon 76 with the bladder wall 52 prevents the introduced distention fluid from leaking substantially from the bladder through the small surgical pathway 72, thereby maintaining the bladder wall 52 in the distended condition and capable of providing sufficient reactive resistance to permit blunt force dilation by the obturator.

Enlarging the small surgical pathway 72 commences as shown in FIG. 17. A scalpel 190 is used to make a few small cuts in the exterior skin 78 extending radially outward from the placement guide 40 in the small surgical pathway 72. Alternatively, the blades 80 on the forward end of the obturator 42 may be extended to make the small cuts, once the forward end of the obturator contacts the exterior skin. These small cuts eliminate the considerable resistance of the exterior skin 78 to enlargement by the forward end of the obturator 42, when the unit-connected obturator 42 and cannula 44 are pushed downward along the taut placement guide 40. The forward end of the obturator 42 moves through the intermediate portion of the abdominal wall 54 between the external skin 78 and the internal fascia layer 82. The point where the internal fascia layer 82 is encountered by the forward end of the obturator 42 is readily detected by an increase in resistance to further forward movement of the obturator 42 along the placement guide 40.

With the forward end of the obturator in contact with the internal fascia layer 82, the blades 80 are extended to cut the fascia layer 82, as shown in FIG. 18. The extended blades 80 cut the fascia layer, and then the blades 80 retract within the forward end of the obturator 42. If necessary, the blades 80 are deployed more than once to cut the internal fascia layer 82. Cutting the fascia layer 82 allows the forward end of the obturator 42 to be moved through the internal fascia layer with a minimum of force. Requiring minimum force to move through the internal fascia layer allows greater control over the surgical process of enlarging the opening for the cannula.

Thereafter, as shown in FIG. 19, the forward end of the obturator 42 is forced through the bladder wall 54 by blunt force dilation. The fluid distending the bladder wall 54 creates sufficient reactive resistance to allow effective the blunt force penetration and dilation of the bladder wall 52. The blunt force dilation enlarges the small surgical pathway 72 through the bladder wall 54 into the enlarged opening 48. The pulling tension force on the placement guide is slightly relaxed to allow the inflated placement balloon 76 to move out of contact with the bladder wall 54 and forward with the forward end of the obturator 42 as the obturator moves through the bladder wall.

The movement of the forward ends of the obturator 42 and cannula 44 into the bladder 50 is accomplished with minimal force due to the blades 80 cutting the internal fascia layer 82. There is minimal risk that pushing force will unintentionally propel the forward end of the obturator into the opposite side of the bladder wall and damage it or possibly even project entirely through the other side of the bladder wall and damage internal organs on the other side of the bladder. Occasionally, in previous techniques, the considerable pushing force required to achieve blunt force penetration through the internal fascia layer may unintentionally propel the forward end of the obturator shaft into adjoining internal organs and tissues when breakthrough of the internal fascia layer occurs. It is very difficult to cease pushing quickly enough after breakthrough occurs to avoid inflicting unintentional damage in previous techniques. Because the inflated placement balloon 76 moves forward with the obturator, the balloon 76 prevents contact or unintended perforation of the back wall of bladder during penetration of the obturator into the bladder. The forward end of the obturator 42 contacts the location where the flexible membrane 92 has been sealed circumferentially around the tube 88 (FIG. 4A) and thereby stops short of contacting the inflated balloon 76. The taut pulling or tension force applied through the placement guide 40 and the inflated balloon 76 assures that the obturator is guided along the placement guide 42 to make the enlarged opening 48 only along the small surgical pathway 72.

After the blunt force penetration through the bladder wall 52, as shown in FIG. 19, the forward ends of the obturator 42 and cannula 44 are moved farther into the bladder 50, as shown in FIG. 20, to locate the flexible membrane 160 of the balloon 84 within the bladder 50. The location of the forward end of the cannula 44 and the flexible membrane 160 is confirmed by viewing through the cystoscope 186.

The stabilization balloon 84 on the forward end of the cannula 44 is then inflated, as shown in FIG. 21. The stabilization balloon 84 is inflated by connecting the syringe 168 to the inflation connector 166 on the cannula 44. Fluid is introduced from the syringe 168 to expand the membrane 160 into the stabilization balloon 84. Thereafter, the rear end of the cannula 44 is pulled upward (as shown) to place the inflated balloon 84 in firm contact with the bladder wall 52 surrounding the enlarged opening 48. Outward force applied on the rear end of the cannula 44 is transferred through the inflated stabilization balloon 84 to hold the bladder wall 52 firmly adjacent to the abdominal wall 54. The retention ring 86 is then moved downward (as shown) along the conduit 64 of the cannula 44 to contact the exterior skin 78. The cannula 44 is located firmly within the enlarged opening 48 as a result of retention from the balloon 84 against the bladder wall 52 and the contact of the retention ring 86 with the exterior skin 78. Alternatively, when the cannula 44' is used, the retention balloon 87 is expanded within the enlarged opening 48 to firmly press against the external skin 78 and internal fascia layer 82 of the abdominal wall 54. The expansion of the retention balloon 87 also has the effect of retaining and stabilizing the cannula 44, or 44', in the enlarged opening 48.

To use the cannula 44 or 44' in its retained position, the obturator 42 and the placement guide 40 are removed from within the central channel 62 of the cannula 44, as shown in FIG. 22. The placement balloon 76 on the forward end of the placement guide 40 is deflated by releasing the check valve in the inflation connector 96 on the rear end of the placement guide. The handle 108 of the housing 106 of the obturator 42 is twisted relative to the cannula 44, thereby separating the tab 158 from the twist lock groove (FIGS. 5 and 9) and allowing the obturator shaft 62 to be removed from within the central channel 62 of the conduit 64 of the cannula 44.

With the obturator 42 and placement guide 40 removed from the cannula 44, the cannula is used in its normal manner for minimally invasive surgical or medical procedures within the bladder 50, as exemplified in FIG. 23. For example, the instrument 56 is inserted through the central channel 62 of the conduit 64 to gain access within the bladder 50. The cannula 44 remains retained in a stabilized position by the retention ring 86 on the exterior skin 78 of the abdominal wall 54 and by the expanded balloon 84 contacting the inner surface of the bladder wall 52 within the bladder 50.

As discussed above, use of the placement guide 40, the obturator 42 and the cannula 44 (or 44') greatly facilitates and improves the placement of the cannula to provide access to the bladder 50. The significance of many of the improvements and advantages of the placement guide 40, the obturator 42 and the cannula 44, and the methodology of the present invention, will become more appreciated after fully comprehending all of the ramifications and improvements of the present invention.

Preferred embodiments of the invention and many of its improvements have been described above with a degree of particularity. The detailed description is of preferred examples of implementing the invention. This detailed description is not necessarily intended to limit the scope of the invention except to the extent set forth in the following claims. The scope of the invention is defined by the claims.

The invention claimed is:

1. A method of enlarging a small surgical pathway through a bladder wall and an abdominal wall to create an enlarged opening and placing a cannula in the enlarged opening, comprising:
   extending an elongated placement guide from the exterior of the abdominal wall through the small surgical pathway until a forward end of the placement guide is located within the bladder;
   inflating a placement balloon on the forward end of the placement guide within the bladder;
   applying pulling tension to the placement guide at the exterior of the abdominal wall to move the inflated placement balloon into contact with the bladder wall and to create a sealing effect from the inflated placement balloon against the bladder wall;
   distending the bladder by introducing fluid into the bladder after the sealing effect is created;
   enlarging the small surgical pathway into the enlarged opening while maintaining the pulling tension on the placement guide by guiding an obturator along the placement guide and through the abdominal wall and the bladder wall, the obturator having a center passage which slidably receives the placement guide; and
   inserting the cannula through the enlarged opening.

2. A method as defined in claim 1, further comprising:
   connecting the obturator and the cannula as a unit by inserting an obturator shaft of the obturator through a central channel of a conduit of the cannula;
   maintaining alignment of the small surgical pathway through the bladder wall and the abdominal wall with the pulling tension applied to the placement guide; and
   guiding the unit-connected obturator and cannula along the placement guide and through the abdominal wall and the bladder wall.

3. A method as defined in claim 2, further comprising:
   cutting skin on the exterior of the abdominal wall to facilitate moving the unit-connected obturator and cannula through the exterior skin of the abdominal wall.

4. A method as defined in claim 2, further comprising:
   extending the placement guide through a center passage extending along the length of the obturator shaft; and
   guiding the unit-connected obturator and cannula along the placement guide with the placement guide extending through the center passage of the obturator.

5. A method as defined in claim 2, further comprising:
   extending at least one blade from a forward end of the obturator while connected to the cannula as the unit to create at least one cut in an internal fascia layer of the abdominal wall when the forward end of the obturator encounters the internal fascia layer.

6. A method as defined in claim 2, further comprising:
   expanding the small surgical pathway into the enlarged opening through the bladder wall by blunt force dilation of the bladder wall with the forward end of the obturator while the inflated placement balloon creates the sealing effect.

7. A method as defined in claim 2, further comprising:
   inflating a stabilization balloon on the forward end of the cannula within the bladder after the cannula extends through the expanded opening; and
   contacting the bladder wall adjacent to the expanded opening with the inflated stabilization balloon while the obturator and the cannula are connected as the unit.

8. A method as defined in claim 1, wherein the applying pulling tension to the placement guide at the exterior of the abdominal wall to move the inflated placement balloon into contact with the bladder maintains the placement guide in a taut position.

9. A method as defined in claim 1, wherein the guiding the obturator through the bladder wall allows the inflated placement balloon to move forward into the bladder as the obturator enters the bladder.

10. A method of enlarging a small surgical pathway through a bladder wall and an abdominal wall to create an enlarged opening and placing a cannula in the enlarged opening, comprising:
    extending an elongated placement guide from the exterior of the abdominal wall through the small surgical pathway until a forward end of the placement guide is located within the bladder;
    inflating a placement balloon on the forward end of the placement guide within the bladder;
    applying pulling tension to the placement guide at the exterior of the abdominal wall to move the inflated placement balloon into contact with the bladder wall and to create a sealing effect from the inflated placement balloon against the bladder wall;
    distending the bladder by introducing fluid into the bladder after the sealing effect is created;
    connecting an obturator and a cannula as a unit by inserting an obturator shaft of the obturator through a central channel of a conduit of the cannula;
    maintaining alignment of the small surgical pathway through the bladder wall and the abdominal wall with the pulling tension applied to the placement guide;
    enlarging the small surgical pathway into the enlarged opening while maintaining the pulling tension on the placement guide by guiding an obturator along the placement guide and through the abdominal wall and the bladder wall;
    guiding the unit-connected obturator and cannula along the placement guide from the exterior skin of the abdominal wall to an internal fascia layer of the abdominal wall;
    extending at least one blade from a forward end of the obturator to create at least one cut in the internal fascia layer of the abdominal wall;
    moving the unit-connected obturator and cannula through the internal fascia layer after creating the cut in the internal fascia layer; and
    inserting the cannula through the enlarged opening.

11. A method as defined in claim 10, further comprising:
    retracting the blade from the forward end of the obturator after creating the cut in the internal fascia layer; and
    enlarging the small surgical pathway into the enlarged opening through the bladder wall by blunt force dilation of the bladder wall with the forward end of the obturator.

12. A method as defined in claim 11, further comprising: moving the forward ends of the unit-connected obturator and cannula into the bladder through the enlarged opening in the bladder wall while simultaneously allowing the inflated placement balloon to move forward with the forward end of the obturator; expanding a stabilization balloon on the forward end of the cannula within the bladder; and withdrawing the cannula until the expanded stabilization balloon contacts the bladder wall adjacent to the expanded opening.

13. A method as defined in claim 12, further comprising:
    deflating the placement balloon after the stabilization balloon contacts the bladder wall; and
    removing the placement guide and the obturator from within the central channel of the conduit of the cannula to provide access through the central channel into the bladder.

14. A method as defined in claim 12, further comprising:
    positioning a retainer on the exterior of the conduit of the cannula in contact with the abdominal wall after the expanded stabilization balloon contacts the bladder wall to maintain and stabilize the cannula within the expanded opening.

15. A method as defined in claim 10, wherein the applying pulling tension to the placement guide at the exterior of the abdominal wall to move the inflated placement balloon into contact with the bladder maintains the placement guide in a taut position.

16. A method as defined in claim 10, wherein the guiding the obturator through the bladder wall allows the inflated placement balloon to move forward into the bladder as the obturator enters the bladder.

17. A method of enlarging a small surgical pathway through a bladder wall and an abdominal wall to create an enlarged opening and placing a cannula in the enlarged opening, comprising:
    forming the small surgical pathway through the bladder wall and the abdominal wall by extending an advancement member from an end of a sound inserted through the urethra into the bladder;
    extending an elongated placement guide from the exterior of the abdominal wall through the small surgical pathway until a forward end of the placement guide is located within the bladder;
    inflating a placement balloon on the forward end of the placement guide within the bladder;
    applying pulling tension to the placement guide at the exterior of the abdominal wall to move the inflated placement balloon into contact with the bladder wall and to create a sealing effect from the inflated placement balloon against the bladder wall;
    distending the bladder by introducing fluid into the bladder after the sealing effect is created;
    enlarging the small surgical pathway into the enlarged opening while maintaining the pulling tension on the placement guide; and
    inserting the cannula through the enlarged opening.

18. A method as defined in claim 1, further comprising:
    extending the placement guide through the small surgical pathway by connecting a forward end of the placement guide to a forward end of the advancement member while the forward end of the advancement member is located at the exterior of the abdominal wall and then withdrawing the advancement member through the small surgical pathway until the placement balloon on the forward end of the placement guide is located within the bladder.

19. A method as defined in claim 18, further comprising:
    locating the placement balloon on the forward end of the placement guide within the bladder by withdrawing the sound and the advancement member and the forward end of the placement guide from the urethra, disconnecting the forward end of the placement guide from the forward end of the advancement member,
    withdrawing the placement guide back through the urethra until the placement balloon at the forward end of the placement guide is located within the bladder, and then inflating the placement balloon in the bladder.

20. A method as defined in claim 1, wherein the applying pulling tension to the placement guide at the exterior of the abdominal wall to move the inflated placement balloon into contact with the bladder maintains the placement guide in a taut position.

* * * * *